US007576106B2

(12) United States Patent
Zhang et al.

(10) Patent No.: US 7,576,106 B2
(45) Date of Patent: *Aug. 18, 2009

(54) PIPERIDINE DERIVATIVES AND METHODS OF USE

(75) Inventors: Penglie Zhang, Foster City, CA (US); Andrew M. K. Pennell, San Francisco, CA (US); Wei Chen, Fremont, CA (US); Kevin Lloyd Greenman, Burlingame, CA (US); Edward J. Sullivan, San Jose, CA (US); Lianfa Li, Palo Alto, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/580,202

(22) Filed: Oct. 11, 2006

(65) Prior Publication Data

US 2007/0093467 A1    Apr. 26, 2007

Related U.S. Application Data

(60) Provisional application No. 60/725,980, filed on Oct. 11, 2005.

(51) Int. Cl.
*C07D 401/06* (2006.01)
*A61K 31/454* (2006.01)

(52) U.S. Cl. .................................. 514/326; 546/211

(58) Field of Classification Search ................ 546/211; 514/326

See application file for complete search history.

(56) References Cited

U.S. PATENT DOCUMENTS

| 4,853,384 | A | 8/1989 | Helsley et al. |
| 6,043,257 | A | 3/2000 | Dominguez et al. |
| 2004/0014783 | A1 | 1/2004 | Rigby et al. |
| 2004/0259914 | A1 | 12/2004 | Ko et al. |
| 2005/0070609 | A1 | 3/2005 | Finke et al. |
| 2005/0143372 | A1 | 6/2005 | Ghosh et al. |
| 2007/0088036 | A1 | 4/2007 | Zhang et al. |

FOREIGN PATENT DOCUMENTS

| JP | 2001019672 | 1/2001 |
| WO | WO 97/38665 A2 | 10/1997 |
| WO | WO 97/38665 A3 | 10/1997 |
| WO | WO 01/90101 | 11/2001 |
| WO | WO 03/000688 A1 | 1/2003 |
| WO | WO 03/013526 A1 | 2/2003 |
| WO | WO 03/037274 | 5/2003 |
| WO | WO 03/105853 | 12/2003 |
| WO | WO 2004/009550 | 1/2004 |
| WO | WO 2004/054974 | 7/2004 |
| WO | WO 2006/066948 | 6/2006 |

OTHER PUBLICATIONS

Xie, et. al. "Identification of novel series of human CCR1 antagonists," Bioorganic & Medicinal Chemistry Letters 2007, doi: 10.1016/j.bmcl.2007.09.068.*
Brown et. al. "Novel CCR1 antagonists with improved metabolic stability" Bioorganic & Medicinal Chemistry Letters 2004, 14, 2175-2179.*
Dominguez et. al. "Design and synthesis of potent and selective 5,6-fused heterocyclic thrombin inhibitors." Bioorganic & Medicinal Chemistry Letters, 1999, 9, 925-930.*
De Lucca et. al. "Discovery and Structure-Activity Relationship of N-(Ureidoalkyl)-Benzyl-Piperidines As Potent Small Molecule CC Chemokine Receptor-3 (CCR3) Antagonists" J. Med. Chem. 2002, 45, 3794-3804.*
Ng et. al. "Discovery of Novel Non-Peptide CCR1 Receptor Antagonists" J. Med. Chem. 1999, 42, 4680-4694.*
International Search Report mailed on Sep. 27, 2007, for PCT Application No. PCT/US06/40014 filed on Oct. 11, 2006, two pages.
Hesselgesser et al., "Identification and Characterization of Small Molecule Functional Antagonists of the CCR1 Chemokine Receptor." *J. Biol. Chem.*, vol. 273, No. 25, pp. 15687-15692, 1998.
Liang et al., "Identification and Characterization of a Potent, Selective, and Orally Active Antagonist of the CC Chemokine Receptor-1." *J. Biol. Chem.*, vol. 275, No. 25, pp. 19000-19008, 2000.
Liang et al., "Species Selectivity of a Small Molecule Antagonist for the CCR1 Chemokine Receptor." *Eur. J. Pharmacol.*, vol. 389, No. 1, pp. 41-49, 2000.
Ng et al., "Discovery of Novel Non-Peptide CCR1 Receptor Antagonists." *J. Med. Chem.*, vol. 42, No. 22, pp. 4680-4694, 1999.

* cited by examiner

*Primary Examiner*—Rita J Desai
*Assistant Examiner*—David K O'Dell
(74) *Attorney, Agent, or Firm*—Townsend and Townsend and Crew LLP

(57) ABSTRACT

Compounds are provided that act as potent antagonists of the CCR1 receptor, and have in vivo anti-inflammatory activity. The compounds are generally monocyclic and bicyclic compounds and are useful in pharmaceutical compositions, methods for the treatment of CCR1-mediated diseases, and as controls in assays for the identification of competitive CCR1 antagonists.

17 Claims, 7 Drawing Sheets

PIPERIDINE DERIVATIVES AND METHODS OF USE

CROSS-REFERENCES TO RELATED APPLICATIONS

This application claims the benefit of Provisional Application Ser. No. 60/725,980, filed Oct. 11, 2005, the disclosure of which is incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The present invention provides compounds, pharmaceutical compositions containing one or more of those compounds or their pharmaceutically acceptable salts, which are effective in inhibiting the binding of various chemokines, such as MIP-1α, leukotactin, MPIF-1 and RANTES, to the CCR1 receptor. As antagonists or modulators for the CCR1 receptor, the compounds and compositions have utility in treating inflammatory and immune disorder conditions and diseases.

Human health depends on the body's ability to detect and destroy foreign pathogens that might otherwise take valuable resources from the individual and/or induce illness. The immune system, which comprises leukocytes (white blood cells (WBCs): T and B lymphocytes, monocytes, macrophages granulocytes, NK cell, mast cells, dendritic cell, and immune derived cells (for example, osteoclasts)), lymphoid tissues and lymphoid vessels, is the body's defense system. To combat infection, white blood cells circulate throughout the body to detect pathogens. Once a pathogen is detected, innate immune cells and cytotoxic T cells in particular are recruited to the infection site to destroy the pathogen. Chemokines act as molecular beacons for the recruitment and activation of immune cells, such as lymphocytes, monocytes and granulocytes, identifying sites where pathogens exist.

Despite the immune system's regulation of pathogens, certain inappropriate chemokine signaling can develop and has been attributed to triggering or sustaining inflammatory disorders, such as rheumatoid arthritis, multiple sclerosis and others. For example, in rheumatoid arthritis, unregulated chemokine accumulation in bone joints attracts and activates infiltrating macrophages and T-cells. The activities of these cells induce synovial cell proliferation that leads, at least in part, to inflammation and eventual bone and cartilage loss (see, DeVries, M. E., et al., *Semin Immunol* 11(2):95-104 (1999)). A hallmark of some demyelinating diseases such as multiple sclerosis is the chemokine-mediated monocyte/macrophage and T cell recruitment to the central nervous system (see, Kennedy, et al., *J. Clin. Immunol.* 19(5):273-279 (1999)). Chemokine recruitment of destructive WBCs to transplants has been implicated in their subsequent rejection. See, DeVries, M. E., et al., ibid. Because chemokines play pivotal roles in inflammation and lymphocyte development, the ability to specifically manipulate their activity has enormous impact on ameliorating and halting diseases that currently have no satisfactory treatment. In addition, transplant rejection may be minimized without the generalized and complicating effects of costly immunosuppressive pharmaceuticals.

Chemokines, a group of greater than 40 small peptides (7-10 kD), ligate receptors expressed primarily on WBCs or immune derived cells, and signal through G-protein-coupled signaling cascades to mediate their chemoattractant and chemostimulant functions. Receptors may bind more than one ligand; for example, the receptor CCR1 ligates RANTES (regulated on activation normal T cell expressed), MIP-1α (macrophage inflammatory protein), MPIF-1/CKβ8, and Leukotactin chemokines (among others with lesser affinities). To date, 24 chemokine receptors are known. The sheer number of chemokines, multiple ligand binding receptors, and different receptor profiles on immune cells allow for tightly controlled and specific immune responses. See, Rossi, et al., *Ann. Rev. Immunol.* 18(1):217-242 (2000). Chemokine activity can be controlled through the modulation of their corresponding receptors, treating related inflammatory and immunological diseases and enabling organ and tissue transplants.

The receptor CCR1 and its chemokine ligands, including, for example MIP-1α, MPIF-1/CKβ8, leukotactin and RANTES, represent significant therapeutic targets (see Saeki, et al., *Current Pharmaceutical Design* 9:1201-1208 (2003)) since they have been implicated in rheumatoid arthritis, transplant rejection (see, DeVries, M. E., et al., ibid.), and multiple sclerosis (see, Fischer, et al., *J Neuroimmunol.* 110 (1-2):195-208 (2000); Izikson, et al., *J. Exp. Med.* 192(7): 1075-1080 (2000); and Rottman, et al., *Eur. J. Immunol.* 30(8):2372-2377 (2000). In fact, function-blocking antibodies, modified chemokine receptor ligands and small organic compounds have been discovered, some of which have been successfully demonstrated to prevent or treat some chemokine-mediated diseases (reviewed in Rossi, et al., ibid.). Notably, in an experimental model of rheumatoid arthritis, disease development is diminished when a signaling-blocking, modified-RANTES ligand is administered (see Plater-Zyberk, et al., *Immunol Lett.* 57(1-3):117-120 (1997)). While function-blocking antibody and small peptide therapies are promising, they suffer from the perils of degradation, extremely short half-lives once administered, and prohibitive expense to develop and manufacture, characteristic of most proteins. Small organic compounds are preferable since they often have longer half lives in vivo, require fewer doses to be effective, can often be administered orally, and are consequently less expensive. Some organic antagonists of CCR1 have been previously described (see, Hesselgesser, et al., *J. Biol. Chem.* 273(25):15687-15692 (1998); Ng, et al., *J. Med. Chem.* 42(22):4680-4694 (1999); Liang, et al., *J. Biol. Chem.* 275(25):19000-19008 (2000); and Liang, et al., *Eur. J. Pharmacol.* 389(1):41-49 (2000)). In view of the effectiveness demonstrated for treatment of disease in animal models (see, Liang, et al., *J. Biol. Chem.* 275(25):19000-19008 (2000)), the search has continued to identify additional compounds that can be used in the treatment of diseases mediated by CCR1 signaling.

BRIEF SUMMARY OF THE INVENTION

The present invention relates to compounds having formula I

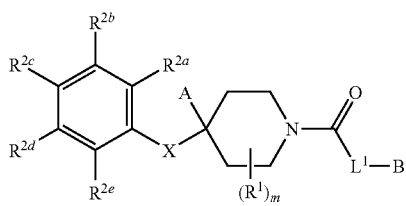

or pharmaceutically acceptable salts and N-oxides thereof; wherein the groups $R^1$, $R^{2a}$, $R^{2b}$, $R^{2c}$, $R^{2d}$, $R^{2e}$, A, B, $L^1$ and X have the meanings provided in detail below.

In addition to the compounds provided herein, the present invention further provides pharmaceutical compositions containing one or more of these compounds, as well as methods for the use of these compounds in therapeutic methods, primarily to treat diseases associated with CCR1, CCR2 and/or CCR3 signalling activity.

DETAILED DESCRIPTION OF THE INVENTION

I. Abbreviation and Definitions

Figure 1:
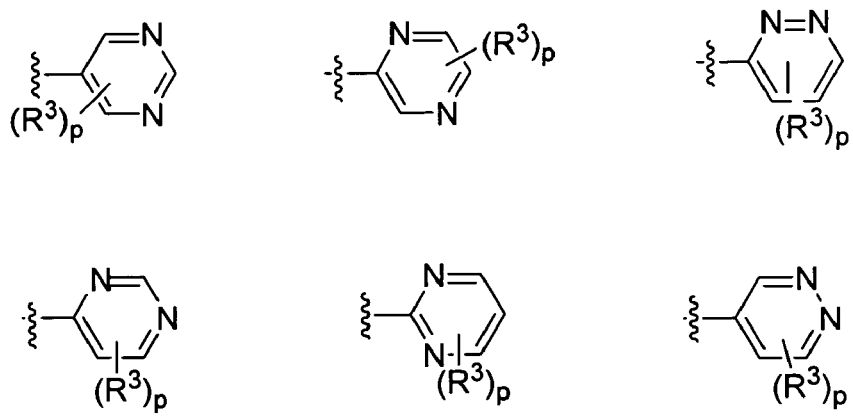
FIG. 1 shows the subformulae of certain preferred B substituents of the invention.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quatemized. The heterocycloalkyl may be a monocyclic, a bicyclic or a polycylic ring system. Non-limiting examples of heterocycloalkyl groups include pyrrolidine, piperidiny, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkyl group can be attached to the remainder of the molecule through a ring carbon or a heteroatom.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

The term "heteroalkyl," by itself or in combination with another term, means, unless otherwise stated, a stable straight or branched chain, unsaturated or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quatemized. The heteroatom(s) O, N, Si and S may be placed at any interior position of the heteroalkyl group. Also, the heteroatom(s) O, N, Si and Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—OCH$_3$, and —CH=CH—N($CH_3$)—$CH_3$. Up to two heteroatoms may be consecutive, such as, for example, —$CH_2$—NH—OCH$_3$ and —$CH_2$—O—Si($CH_3$)$_3$.

The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—, —O—$CH_2$—CH=CH—, —$CH_2$—CH=C(H)$CH_2$—O—$CH_2$— and —S—$CH_2$—C≡C—. For heteroalkylene groups, heteroatoms can also occupy either or both of the chain termini (e.g., alkyleneoxy, alkylenedioxy, alkyleneamino, alkylenediamino, and the like).

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like).

The above terms (e.g., "alkyl," "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below, while the term "alkyl" and related aliphatic radicals is meant to refer to unsubstituted version, unless indicated to be substituted.

Substituents for the alkyl radicals (including those groups often referred to as alkylene, alkenyl, alkynyl and cycloalkyl) can be a variety of groups selected from: -halogen, —OR', —NR'R", —SR', —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R''' each independently refer to hydrogen, unsubstituted $C_{1-8}$ alkyl, unsubstituted heteroalkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro ($C_1$-$C_4$)alkoxy, and perfluoro ($C_1$-$C_4$)alkyl, in a number ranging from zero to the total number of open valences on the aromatic ring system; and where R', R" and R''' are independently selected from hydrogen, $C_{1-8}$ alkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula —T—C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'—and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

As used herein, a wavy line, "~",that intersects a single, double or triple bond in any chemical structure depicted herein, represent the point attachment of the single, double, or triple bond to the remainder of the molecule.

"Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis,* 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (BOC), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Amino acid coupling reagent" refers to a reagent, such as HATU, etc., that will react with the carboxylic acid group of an amino acid to form an activated intermediate that can be used to condense with a wide variety of nucleophiles, for example, amines, alcohols and thiols, to produce other esters, thioesters or amides groups.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

II. General

The present invention derives from the discovery that compounds of formula I act as potent antagonists of the CCR1 receptor. The compounds have in vivo anti-inflammatory activity. Accordingly, the compounds provided herein are useful in pharmaceutical compositions, methods for the treatment of CCR1-mediated diseases, and as controls in assays for the identification of competitive CCR1 antagonists.

III. Compounds

In one aspect, the present invention provides for compounds having formula I

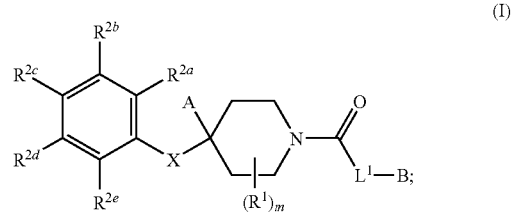

and pharmaceutically acceptable salts and N-oxides thereof.

In formula I; the subscript m is an integer of from 0 to 4, and each $R^1$ is independently selected from the group consisting of $C_{1-8}$ alkyl, $C_{1-8}$ haloalkyl, $C_{3-6}$ cycloalkyl, —$CO_2R^a$, —$SO_2R^a$, —$OR^a$, —$COR^a$, —$CONR^aR^b$, —$NR^aR^b$, —$NR^aCOR^b$, —$CONR^aR^b$, —$NR^aS(O)_2R^b$, $S(O)_2NR^aR^b$, $S(O)_2R^a$, —$X^1CO_2R^a$, —$X^1SO_2R^a$, —$X^1OR^a$, —$X^1COR^a$, —$X^1CONR^aR^b$, —$X^1NR^aR^b$, —$X^1NR^aCOR^b$, —$X^1CONR^aR^b$, $X^1NR^aS(O)_2R^b$, $X^1S(O)_2NR^aR^b$ and $X^1S(O)_2R^a$, wherein $X^1$ is $C_{1-4}$ alkylene, $C_{2-4}$ alkenylene, or $C_{2-4}$ alkynylene, and each $R^a$ and $R^b$ is independently selected from the group consisting of hydrogen, $C_{1-8}$ alkyl, $C_{1-8}$ haloalkyl and $C_{3-6}$ cycloalkyl, or optionally, when $R^a$ and $R^b$ are attached to the same nitrogen atom may be combined to form a 4- to 7-membered ring having from 0-2 additional heteroatoms as members selected from N, O or S; and wherein any two $R^1$ substituents attached to the same or different carbon atoms are optionally cyclized to form a 3- to 7-membered ring; and wherein the aliphatic portions of each $R^1$ substituent is optionally substituted with from one to three members selected from the group consisting of —OH, —OR$^m$, —OC(O)NHR$^m$, —OC(O)N(R$^m$)$_2$, —SH, —SR$^m$, —S(O)R$^m$, —S(O)$_2$R$^m$, —SO$_2$NH$_2$, —S(O)$_2$NHR$^m$, —S(O)$_2$N(R$^m$)$_2$, —NHS(O)$_2$R$^m$, —NR$^m$S(O)$_2$R$^m$, —C(O)NH$_2$, —C(O)NHR$^m$, —C(O)N(R$^m$)$_2$, —C(O)R$^m$, —NHC(O)R$^m$, —NR$^m$C(O)R$^m$, —NHC(O)NH$_2$, —NR$^m$C(O)NH$_2$, —NR$^m$C(O)NHR$^m$, —NHC(O)NHR$^m$, —NR$^m$C(O)N(R$^m$)$_2$, —NHC(O)N(R$^m$)$_2$, —CO$_2$H, —CO$_2$R$^m$, —NHCO$_2$R$^m$, —NR$^m$CO$_2$R$^m$, —CN, —NO$_2$, —NH$_2$, —NHR$^m$, —N(R$^m$)$_2$, —NR$^m$S(O)NH$_2$ and —NR$^m$S(O)$_2$NHR$^m$, wherein each R$^m$ is independently an unsubstituted $C_{1-6}$ alkyl.

The symbols $R^{2a}$, $R^{2b}$, $R^{2c}$, $R^{2d}$ and $R^{2e}$ are each independently selected from the group consisting of hydrogen, halogen, —OR$^c$, —OC(O)R$^c$, —NR$^c$R$^d$, —SR$^c$, —R$^e$, —CN, —NO$_2$, —CO$_2$R$^c$, —CONR$^c$R$^d$, —C(O)R$^c$, —OC(O)NR$^c$R$^d$, —NR$^d$C(O)R$^c$, —NR$^d$C(O)$_2$R$^e$, —NR$^c$—C(O)NR$^c$R$^d$, —NH—C(NH$_2$)=NH, —NR$^e$C(NH$_2$)=NH, —NH—C(NH$_2$)=NR$^e$, —NH—C(NHR$^e$)=NH, —NR$^e$C(NHR$^e$)=NH, —NR$^e$C(NH$_2$)=NR$^e$, —NH—C(NHR$^e$)=NR$^e$, —NH—C(NR$^e$R$^e$)=NH, —S(O)R$^e$, —S(O)$_2$R$^e$, —NR$^c$S(O)$_2$R$^e$, —S(O)$_2$NR$^c$R$^d$, —N$_3$, —C(NOR$^c$)R$^d$, —C(NR$^c$W)=NW, —N(W)C(R$^c$)=NW, —NR$^c$C(S)NR$^c$R$^d$, —X$^2$C(NOR$^c$)R$^d$, —X$^2$C(NR$^c$W)=NW, —X$^2$N(W)C(R$^c$)=NW, —X$^2$NR$^c$C(S)NR$^c$R$^d$, —X$^2$OR$^c$, —O—X$^2$OR$^c$, —X$^2$OC(O)R$^c$, —X$^2$NR$^c$R$^d$, —O—X$^2$NR$^c$R$^d$, —X$^2$SR$^c$, —X$^2$CN, —X$^2$NO$_2$, —X$^2$CO$_2$R$^c$, —O—X$^2$CO$_2$R$^c$, —X$^2$CONR$^c$R$^d$, —O—X$^2$CONR$^c$R$^d$, —X$^2$C(O)R$^c$, —X$^2$OC(O)NR$^c$R$^d$, —X$^2$NR$^d$C(O)R$^c$, —X$^2$NR$^d$C(O)$_2$R$^e$, —X$^2$NR$^c$C(O)NR$^c$R$^d$, —X$^2$NH—C(NH$_2$)=NH, X$^2$NR$^e$C(NH$_2$)=NH, —X$^2$NH—C(NH$_2$)=NR$^e$, —X$^2$NH—C(NHR$^e$)=NH, —X$^2$S(O)R$^e$, —X$^2$S(O)$_2$R$^e$, —X$^2$NR$^c$S(O)$_2$R$^e$, —X$^2$S(O)$_2$NR$^c$R$^d$, —X$^2$N$_3$, —NR$^d$—X$^2$OR$^c$, —NR$^d$—X$^2$NR$^c$R$^d$, —NR$^d$—X$^2$CO$_2$R$^c$, and —NR$^d$—X$^2$CONR$^c$R$^d$, wherein W is selected from R$^c$, —CN, —CO$_2$R$^e$ and —NO$_2$, and wherein X$^2$ is $C_{1-4}$ alkylene, $C_{2-4}$ alkenylene, $C_{2-4}$ alkynylene or $C_{1-4}$ heteroalkylene; and each R$^c$ and R$^d$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, or optionally R$^c$ and R$^d$ when attached to the same nitrogen atom can be combined to form a five or six-membered ring having from 0 to 2 additional heteroatoms as ring members selected from N, O or S; and each R$^e$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, and each of R$^c$, R$^d$ and R$^e$ is optionally further substituted with from one to three members selected from the group consisting of —OH, —OR$^n$, —OC(O)NHR$^n$, —OC(O)N(R$^n$)$_2$, —SH, —SR$^n$, —S(O)R$^n$, —S(O)$_2$R$^n$, —SO$_2$NH$_2$, —S(O)$_2$NHR$^n$, —S(O)$_2$N(R$^n$)$_2$, —NHS(O)$_2$R$^n$, —NR$^n$S(O)$_2$R$^n$, —C(O)NH$_2$, —C(O)NHR$^n$, —C(O)N(R$^n$)$_2$, —C(O)R$^n$, —NHC(O)R$^n$, —NR$^n$C(O)R$^n$, —NHC(O)NH$_2$, —NR$^n$C(O)NH$_2$, —NR$^n$C(O)NHR$^n$, —NHC(O)NHR$^n$, —NR$^n$C(O)N(R$^n$)$_2$, —NHC(O)N(R$^n$)$_2$, —CO$_2$H, —CO$_2$R$^n$, —NHCO$_2$R$^n$, —NR$^n$CO$_2$R$^n$, —CN, —NO$_2$, —NH$^2$, —NHR$^n$, —N(R$^n$)$_2$, —NR$^n$S(O)NH$_2$ and —NR$^n$S(O)$_2$NHR$^n$, wherein each R$^n$ is independently an unsubstituted $C_{1-6}$ alkyl; and at least one of $R^{2a}$, $R^{2b}$, $R^{2c}$, $R^{2d}$ and $R^{2e}$ is other than hydrogen.

The letter B represents a heteroaryl ring or ring system having 1-4 heteroatoms as ring members selected from the group consisting of N, O and S; wherein B is substituted with 0 to 5 $R^3$ substitutents, and at each occurrence, $R^3$ is independently selected from the group consisting of halogen, —OR$^f$, —OC(O)R$^f$, —NR$^f$R$^g$, —SR$^f$, —R$^h$, —CN, —NO$_2$, —CO$_2$R$^f$, —CONR$^f$R$^g$, —C(O)R$^f$, —OC(O)NR$^f$R$^g$, —NR$^g$C(O)R$^f$, —NR$^g$C(O)$_2$R$^h$, —NR$^f$—C(O)NR$^f$R$^g$, —NH—C(NH$_2$)=NH, —NR$^h$C(NH$_2$)=NH, —NH—C(NH$_2$)=NR$^h$, —NH—C(NHR$^h$)=NH, —S(O)R$^h$, —S(O)$_2$R$^h$, —NR$^f$S(O)$_2$R$^h$, —S(O)$_2$NR$^f$R$^g$, —NR$^f$S(O)$_2$NR$^f$R$^g$, —N$_3$, —C(O)NR$^f$S(O)R$^h$, —C(O)NR$^f$S(O)$_2$R$^h$, —P=O(OR$^f$)(OR$^g$), —X$^3$OR$^f$, —X$^3$OC(O)R$^f$, —X$^3$NR$^f$R$^g$, —X$^3$SR$^f$, —X$^3$CN, —X$^3$NO$_2$, —X$^3$CO$_2$R$^f$, —X$^3$CONR$^f$R$^g$, —X$^3$C(O)R$^f$, —X$^3$OC(O)NR$^f$R$^g$, —X$^3$NR$^g$C(O)R$^f$, —X$^3$NR$^g$C(O)$_2$R$^h$, —X$^3$NR$^f$—C(O)NR$^f$R$^g$, —X$^3$NH—C(NH$_2$)=NH, —X$^3$NR$^h$C(NH$_2$)=NH, —X$^3$NH—C(NH$_2$)=NR$^h$, —X$^3$NH—C(NHR$^h$)=NH, —X$^3$S(O)R$^h$, —X$^3$S(O)$_2$R$^h$, —X$^3$NR$^f$S(O)$_2$R$^h$, —X$^3$S(O)$_2$NR$^f$R$^g$, —X$^3$C(O)NR$^f$S(O)$_2$R$^h$, —X$^3$C(O)NR$^f$S(O)R$^h$, —X$^3$P=O(OR$^f$)(OR$^g$), —Y, —X$^3$Y and —X$^3$N$_3$, wherein Y is a five to ten-membered aryl, heteroaryl or heterocycloalkyl ring, optionally substituted with from one to three substitutents selected from the group consisting of halogen, —OR$^f$, —NR$^f$R$^g$, —R$^h$, —SR$^f$, —CN, —NO$_2$, —CO$_2$R$^f$, —CONR$^f$R$^g$, —C(O)R$^f$, —NR$^g$C(O)R$^f$, —S(O)R$^h$, —S(O)$_2$R$^h$, —NR$^f$S(O)$_2$R$^h$, —S(O)$_2$NR$^f$R$^g$, —C(O)NR$^f$S(O)$_2$R$^h$, —C(O)NR$^f$S(O)R$^h$, —P=O(OR$^f$)(OR$^g$), —X$^3$OR$^f$, —X$^3$NR$^f$R$^g$, —X$^3$NR$^f$S(O)$_2$R$^h$, —X$^3$CO$_2$R$^f$, —X$^3$CONR$^f$R$^g$, —X$^3$C(O)R$^f$, —X$^3$NR$^g$C(O)R$^f$, —X$^3$S(O)R$^h$, —X$^3$S(O)$_2$R$^h$, —X$^3$C(O)NR$^f$S(O)$_2$R$^h$, —X$^3$C(O)NR$^f$S(O)$_2$R$^h$, —X$^3$P=O(OR$^f$)(OR$^g$) and —X$^3$S(O)$_2$NR$^f$R$^g$, any two $R^3$ substituents on adjacent atoms may be optionally combined to form a 5- to 6-membered ring optionally having 1-2 heteroatom ring members selected from N, O and S; each $X^3$ is independently selected from the group consisting of $C_{1-4}$ alkylene, $C_{2-4}$ alkenylene, $C_{2-4}$ alkynylene and $C_{1-4}$ heteroalkylene; each R$^f$ and R$^g$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl and aryloxy-$C_{1-4}$ alkyl; and each R$^h$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl and aryloxy-$C_{1-4}$ alkyl, wherein the aliphatic portions of $X^3$, R$^f$, R$^g$ and R$^h$ are optionally further substituted with from one to three members selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$^2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$, wherein R$^o$ is unsubstituted $C_{1-6}$ alkyl; and B is other than pyridine, quinoline or isoquinoline.

The symbol $L^1$ represents a bond, a $C_{1-4}$ alkylene, a $C_{1-4}$ alkenylene or a $C_{1-4}$ heteroalkylene linking group, each optionally substituted with from 1 to 4 $R^4$ groups wherein $R^4$ at each occurrence is independently selected from the group consisting of phenyl, —R$^k$, —X$^4$OR$^i$, —X$^4$OC(O)R$^i$, —X$^4$NR$^i$R$^j$, —X$^4$SR$^i$, —X$^4$CN or —X$^4$NO$_2$, wherein $X^4$ is selected from the group consisting of $C_{1-4}$ alkylene, $C_{2-4}$ heteroalkylene, $C_{2-4}$ alkenylene and $C_{2-4}$ alkynylene and each R$^i$ and R$^j$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, and each R$^k$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl.

The letter A represents a substituent selected from the group consisting of hydrogen, aryl, heteroaryl, aryl-X$^5$—, heteroaryl-$X^5$—, Z or Z—$X^5$—, wherein Z is selected from the group consisting of —$OR^q$, —$OC(O)R^q$, —$NR^qR^r$, —$SR^q$, —$R^s$, —CN, —$NO_2$, —$CO_2R^q$, —$CONR^qR^r$, —$C(O)R^q$, —$C(O)R^s$, —$OC(O)NR^qR^r$, —$NR^rC(O)R^q$, —$NR^rC(O)_2R^s$, —$NR^q$—$C(O)NR^qR^r$, —NH—$C(NH_2)$=NH, —$NR^sC(NH_2)$=NH, —NH—$C(NH_2)$=$NR^s$, —NH—$C(NHR^s)$=NH, —$NR^sC(NHR^s)$=NH, —$NR^sC(NH_2)$=$NR^s$, —NH—$C(NHR^s)$=$NR^s$, —NH—$C(NR^sR^s)$=NH, —$S(O)R^s$, —$S(O)_2R^s$, —$NR^qS(O)_2R^s$, —$S(O)_2NR^qR^r$, —$N_3$, —$C(NOR^q)R^r$, —$C(NR^qW)$=NW, —$N(W)C(R^q)$=NW, —$NR^qC(S)NR^qR^r$, —$C(NOR^q)R^r$, —$C(NR^qW)$=NW, —$N(W)C(R^q)$=NW, —$NR^qC(S)NR^qR^r$ and —$NR^qS(O)NR^qR^r$, wherein W is selected from $R^q$, —CN, —$CO_2R^s$ and —$NO_2$, and wherein $X^5$ is $C_{1-4}$ alkylene, $C_{1-4}$ heteroalkylene, $C_{2-6}$ alkenylene and $C_{2-6}$ alkynylene; and each $R^q$ and $R^r$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, or optionally $R^q$ and $R^r$ when attached to the same nitrogen atom can be combined with the nitrogen atom to form a four-, five- or six-membered ring having from 0 to 2 additional heteroatoms as ring members; and each $R^s$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, and each of $X^5$, $R^q$, $R^r$ and $R^s$ is optionally further substituted with from one to three members selected from the group consisting of —OH, —$OR^t$, —$OC(O)NHR^t$, —$OC(O)N(R^t)_2$, —SH, —$SR^t$, —$S(O)R^t$, —$S(O)_2R^t$, —$SO_2NH_2$, —$S(O)_2NHR^t$, —$S(O)_2N(R^t)_2$, —$NHS(O)_2R^t$, —$NR^tS(O)_2R^t$, —$C(O)NH_2$, —$C(O)NHR^t$, —$C(O)N(R^t)_2$, —$C(O)R^t$, —$NHC(O)R^t$, —$NR^tC(O)R^t$, —$NHC(O)NH_2$, —$NR^tC(O)NH_2$, —$NR^tC(O)NHR^t$, —$NHC(O)NHR^t$, —$NR^tC(O)N(R^t)_2$, —$NHC(O)N(R^t)_2$, —$CO_2H$, —$CO_2R^t$, —$NHCO_2R^t$, —$NR^tCO_2R^t$, —CN, —$NO_2$, —$NH_2$, —$NHR^t$, —$N(R^t)_2$, —$NR^tS(O)NH_2$ and —$NR^tS(O)_2NHR^t$, wherein each $R^t$ is independently an unsubstituted $C_{1-6}$ alkyl.

The letter X represents a linking group selected from the group consisting of —$C(R^u)_2$—, —O—, and —$NR^u$, wherein each $R^u$ is independently selected from the group consisting of hydrogen, $C_{1-8}$ alkyl, $C_{1-8}$ haloalkyl and $C_{3-6}$ cycloalkyl, is optionally further substituted with from one to three members selected from the group consisting of —OH, oxo, —$OR^v$, —$OC(O)NHR^v$, —$OC(O)N(R^v)_2$, —SH, —$SR^v$, —$S(O)R^v$, —$S(O)_2R^v$, —$SO_2NH_2$, —$S(O)_2NHR^v$, —$S(O)_2N(R^v)_2$, —$NHS(O)_2R^v$, —$NR^vS(O)_2R^v$, —$C(O)NH_2$, —$C(O)NHR^v$, —$C(O)N(R^v)_2$, —$C(O)R^v$, —$NHC(O)R^v$, —$NR^vC(O)R^v$, —$NHC(O)NH_2$, —$NR^vC(O)NH_2$, —$NR^vC(O)NHR^v$, —$NHC(O)NHR^v$, —$NR^vC(O)N(R^v)_2$, —$NHC(O)N(R^v)_2$, —$CO_2H$, —$CO_2R^v$, —$NHCO_2R^v$, —$NR^vCO_2R^v$, —CN, —$NO_2$, —$NH_2$, —$NHR^v$, —$N(R^v)_2$, —$NR^vS(O)NH_2$ and —$NR^vS(O)_2NHR^v$, wherein each $R^v$ is independently an unsubstituted $C_{1-6}$ alkyl or $C_{1-6}$ haloalkyl.

For the compounds of the present invention, the molecular weight is typically less than or equal to 700. In some instances, preferred compounds have a molecular weight of less than 600, more preferably less than 550. In one group of particularly preferred embodiments, the compounds have a molecular weight of from 400 to 550. The compounds of the present invention typically have a calculated octanol/water partition coefficient of from 1.0 to 5.5, more preferably from 1.0 to 4.0.

The $R^1$ Substituent:

In some embodiments, the subscript m is 0, 1 or 2. When two $R^1$ substituents are provided, each is independently selected. In one group of embodiments, when one or two $R^1$ substituents are present, they are selected from $C_{1-6}$ alkyl, $C_{1-3}$ haloalkyl, $C_{3-6}$ cycloalkyl, —$CO_2R^a$, —$SO_2R^a$, —$OR^a$, $COR^a$, —$CONR^aR^b$, —$NR^aR^b$, —$NR^aCOR^b$, —$NR^aS(O)_2R^b$, $S(O)_2NR^aR^b$, $S(O)_2R^a$, —$X^1CO_2R^a$, —$X^1SO_2R^a$, —$X^1OR^a$, —$X^1COR^a$, —$X^1CONR^aR^b$, —$X^1NR^aR^b$, —$X^1NR^aCOR^b$, —$X^1CONR^aR^b$, $X^1NR^aS(O)_2R^b$, $X^1S(O)_2NR^aR^b$ and $X^1S(O)_2R^a$, wherein $X^1$ is $C_{1-2}$ alkylene, and each $R^a$ and $R^b$ is independently selected from the group consisting of hydrogen, $C_{1-4}$ alkyl, $C_{1-3}$ haloalkyl and $C_{3-6}$ cycloalkyl, wherein $R^a$ and $R^b$ when attached to the same nitrogen atom may be combined to form a 5- or 6-membered ring. In another group of embodiments, $R^1$ is selected from $C_{1-6}$ alkyl, —$CO_2R^a$ and —$CONR^aR^b$.

The $R^2$ Substituents ($R^{2a}$, $R^{2b}$, $R^{2c}$, $R^{2d}$ and $R^{2e}$):

In some embodiments, the $R^2$ substituents are independently selected from hydrogen, halogen, $C_{1-6}$ alkyl, $C_{1-3}$ haloalkyl, $C_{3-6}$ cycloalkyl, —$CO_2R^c$, —$S(O)_2R^e$, —$OR^c$, —$C(O)R^c$, —$CONR^cR^d$ and —$S(O)_2NR^cR^d$. In some embodiments each of $R^{2a}$, $R^{2b}$, $R^{2c}$, $R^{2d}$ and $R^{2e}$ is independently selected from hydrogen, halogen, $C_{1-6}$ alkyl and $C_{1-3}$ haloalkyl.

In some embodiments, $R^{2a}$ is a substituent selected from the group consisting of hydrogen, halogen, cyano, heteroaryl, —$NO_2$, —$CO_2R^c$, —$CONR^cR^d$, —$C(O)R^c$, —$S(O)R^e$, —$S(O)_2R^e$, —$R^e$, —$C(NOR^c)R^d$, —$C(NR^cW)$=NW, —$N(W)C(R^c)$=NW, —$X^2C(NOR^c)R^d$, —$X^2C(NR^cW)$=NW, —$X^2N(W)C(R^c)$=NW, —$X^2NR^cR^d$, —$X^2SR^c$, —$X^2CN$, —$X^2NO_2$, —$X^2CO_2R^c$, —$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^cR^d$, —$X^2NH$—$C(NH_2)$=NH, —$X^2NR^eC(NH_2)$=NH, —$X^2NH$—$C(NH_2)$=$NR^e$, —$X^2NH$—$C(NHR^e)$=NH, —$X^2S(O)R^e$, —$X^2S(O)_2R^e$, —$X^2NR^cS(O)_2R^e$, —$X^2S(O)_2NR^cR^d$ and —$X^2N_3$. The symbols $R^{2b}$ and $R^{2e}$ are each hydrogen; and $R^{2c}$ and $R^{2d}$ are each independently selected from the group consisting of hydrogen halogen, —$OR^c$, —$SR^c$, —$R^e$, —CN, —$NO_2$, —$CO_2R^c$, —$C(O)R^c$, —$NR^dC(O)R^c$, $NR^dC(O)_2R^e$, —$S(O)_2R^e$, —$S(O)_2NR^cR^d$, —$X^2OR^c$, —O—$X^2OR^c$, —$X^2NR^cR^d$, —O—$X^2NR^cR^d$ and —$NR^d$—$X^2CO_2R^c$.

In still other embodiments, the symbols $R^{2a}$, $R^{2b}$, $R^{2d}$ and $R^{2e}$ are each hydrogen; and $R^{2c}$ is selected from the group consisting of halogen, —$OR^c$, —$SR^c$, —$R^e$, —CN, —$NO_2$, —$CO_2R^c$, —$C(O)R^c$, —$NR^dC(O)R^c$, —$NR^dC(O)_2R^e$, —$S(O)_2R^e$, —$S(O)_2NR^cR^d$, —$X^2OR^c$, —O—$X^2OR^c$, —$X^2NR^cR^d$, —O—$X^2NR^cR^d$ and —$NR^d$—$X^2CO_2R^c$. In certain embodiments, $R^{2c}$ is fluoro, chloro, bromo or iodo.

In yet another group of embodiments, the symbols $R^{2a}$, $R^{2b}$, $R^{2e}$ are each hydrogen; and $R^{2c}$ and $R^{2d}$ are each independently selected from the group consisting of hydrogen halogen, —$OR^c$, —$SR^c$, —$R^e$, —CN, —$NO_2$, —$CO_2R^c$, —$C(O)R^c$, —$NR^dC(O)R^c$, $NR^dC(O)_2R^e$, —$S(O)_2R^e$, —$S(O)_2NR^cR^d$, —$X^2OR^c$, —O—$X^2OR^c$, —$X^2NR^cR^d$, —O—$X^2NR^cR^d$ and —$NR^d$—$X^2CO_2R^c$.

In still another group of embodiments, the symbols $R^{2a}$, $R^{2b}$, $R^{2d}$ and $R^{2e}$ are each hydrogen and $R^{2c}$ is selected from the group consisting of halogen, —$OR^c$, —$SR^c$, —$R^e$, —CN, —$NO_2$.

The B Substituent:

In certain embodiment of compounds having Formula I the symbol B is a heteroaryl group selected from the group consisting of:

i) 5- to 6-membered heteroaryl ring having from 1-4 heteroatoms as ring members selected from the group consisting of N, O and S, and is substituted with 1-4 $R^3$ substituents; and ii) 8- to 10-membered bicyclic heteroaryl ring having from 1-4 heteroatoms as ring members selected from the group consisting of N, O and S, and is substituted with 1-4 $R^3$ substituents.

In one embodiment of formula I, B can be attached to the remainder of the molecule through a carbon atom. Alternatively, when B is selected from the group set forth in (i) or (ii) above, then B can be attached to the remainder of the molecule through a nitrogen atom or a carbon atom.

In a second embodiment of compounds having formula I, the symbol B is an optionally substituted member selected from the group consisting of pyrimidinyl, pyrazinyl and pyridazinyl. In another instance, B is an optionally substituted member selected from the group consisting of tetrazolyl, triazolyl, imidazolyl, pyrrolyl, pyrazolyl, oxazolyl, thiazolyl, isothiazolyl, isoxazolyl, furanyl, oxadiazolyl and thienyl. In yet another instance, the symbol B is an optionally substituted member selected from the group consisting of benzimidazolyl, benzopyrazolyl, benzotriazolyl, benzotetrazolyl, benzooxazolyl, benzoisoxazolyl, benzooxadiazolyl, benzothienyl, benzoisothiazolyl, benzofuranyl, quinazolinyl, quinoxalinyl, naphthyridinyl, pyrimidinopyridinyl, pyridazinopyridinyl, pyrazinopyridinyl, pyridinopyrimidinyl, pyrimidinopyrimidinyl, pyridazinopyrimidinyl, pyrazinopyrimidinyl, pyridinopyridazinyl, pyrimidinopyridazinyl, pyridazinopyridazinyl, pyrazinopyridazinyl, pyridinopyrazinyl, pyrimidinopyrazinyl, pyridazinopyrazinyl, pyrazinopyrazinyl, pyridinoimidazolyl, purinyl, pyridazinoimidazolyl, pyrazinoimidazolyl, pyridinooxazolyl, pyrimidinooxazolyl, pyridazinooxazolyl, pyrazinooxazolyl, pyridinoisoxazolyl, pyrimidinoisoxazolyl, pyridazinoisoxazolyl, pyrazinoisoxazolyl, pyridinooxathiadiazolyl, pyrimidinooxathiadiazolyl, pyridazinooxathiadiazolyl, pyrazinooxathiadiazolyl, pyridinooxathiazolyl, pyrimidinooxathiazolyl, pyridazinooxathiazolyl, pyrazinooxathiazolyl, pyridinothiazolyl, pyrimidinothiazolyl, pyridazinothiazolyl, pyrazinothiazolyl, pyridinopyrazolyl, pyrimidinopyrazolyl, pyridazinopyrazolyl, pyrazinopyrazolyl, pyridinopyrrolyl, pyrimidinopyrrolyl, pyridazinopyrrolyl and pyrazinopyrrolyl.

In another embodiment in compounds having Formula I, the symbol B has the formula selected from the group set forth in FIG. 1. In FIG. 1, the $R^3$ substituent at each occurrence, is independently selected from the group consisting of halogen, —$OR^f$, —$OC(O)R^f$, —$NR^fR^g$, —$SR^f$, —$R^h$, —CN, —$NO_2$, —$CO_2R^f$, —$CONR^fR^g$, —$C(O)R^f$, —$OC(O)NR^fR^g$, —$NR^gC(O)R^f$, —$NR^gC(O)_2R^h$, —$NR^f$—$C(O)NR^fR^g$, —NH—$C(NH_2)$=NH, —$NR^hC(NH_2)$=NH, —NH—$C(NH_2)$=$NR^h$, —NH—$C(NHR^h)$=NH, —$S(O)R^h$, —$S(O)_2R^h$, —$NR^fS(O)_2R^h$, —$S(O)_2NR^fR^g$, —$NR^fS(O)_2NR^fR^g$, —$N_3$, —$C(O)NR^fS(O)R^h$, —$C(O)NR^fS(O)_2R^h$, —P=O$(OR^f)(OR^g)$, —$X^3OR^f$, —$X^3OC(O)R^f$, —$X^3NR^fR^g$, —$X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^f$—$C(O)NR^fR^g$, —$X^3NH$—$C(NH_2)$=NH, —$X^3NR^hC(NH_2)$=NH, —$X^3NH$—$C(NH_2)$=$NR^h$, —$X^3NH$—$C(NHR^h)$=NH, —$X^3S(O)R^h$, —$X^3S(O)_2 R^h$, —$X^3NR^fS(O)_2R^h$, —$X^3S(O)_2NR^fR^g$, —$X^3C(O)NR^fS(O)_2R^h$, —$X^3C(O)NR^fS(O)R^h$, —$X^3P$=O$(OR^f)(OR^g)$, —Y, —$X^3Y$ and —$X^3N_3$, wherein Y is a five to ten-membered aryl, heteroaryl or heterocycloalkyl ring, optionally substituted with from one to three substituents selected from the group consisting of halogen, —$OR^f$, —$NR^fR^g$, —$R^h$, —$SR^f$, —CN, —$NO_2$, —$CO_2R^f$, —$CONR^fR^g$, —$C(O)R^f$, —$NR^gC(O)R^f$, —$S(O)R^h$, —$S(O)_2R^h$, —$NR^fS(O)_2R^h$, —$S(O)_2NR^fR^g$, —$C(O)NR^fS(O)_2R^h$, —$C(O)NR^fS(O)R^h$, —P=O$(OR^f)(OR^g)$, —$X^3OR^f$, —$X^3NR^fR^g$, —$X^3NR^fS(O)_2R^h$, —$X^3CO_2R^f$, —$X^3CONR^fR^g$, —$X^3C(O)R^f$, —$X^3NR^gC$(O)$R^f$, —$X^3S(O)R^h$, —$X^3S(O)_2R^h$, —$X^3C(O)NR^fS(O)_2R^h$, —$X^3C(O)NR^fS(O)_2R^h$, —$X^3P$=O$(OR^f)(OR^g)$ and —$X^3S(O)_2NR^fR^g$. In addition any two $R^3$ substituents on adjacent atoms may be optionally combined to form a 5- to 6-membered ring optionally having 1-2 heteroatom ring members selected from N, O and S. Each $X^3$ is independently selected from the group consisting of $C_{1-4}$ alkylene, $C_{2-4}$ alkenylene, $C_{2-4}$ alkynylene and $C_{1-4}$ heteroalkylene; each $R^f$ and $R^g$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl and aryloxy-$C_{1-4}$ alkyl; and each $R^h$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl and aryloxy-$C_{1-4}$ alkyl, wherein the aliphatic portions of $X^3$, $R^f$, $R^g$ and $R^h$ are optionally further substituted with from one to three members selected from the group consisting of —OH, —$OR^o$, —OC(O)$NHR^o$, —OC(O)N$(R^o)_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R_o$, —$NR_oS(O)_2R^o$, —$C(O)NH_2$, —$C(O)NHR^o$, —$C(O)N(R_o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —$NR^oCO_2R^o$, —CN, —$NO_2$, —$NH_2$, —$NHR^o$, —$N(R^o)_2$, —$NR^oS(O)NH_2$ and —$NR^oS(O)_2NHR^o$, wherein $R^o$ is unsubstituted $C_{1-6}$ alkyl. The subscript p is an integer from 0-5.

Figure 2:
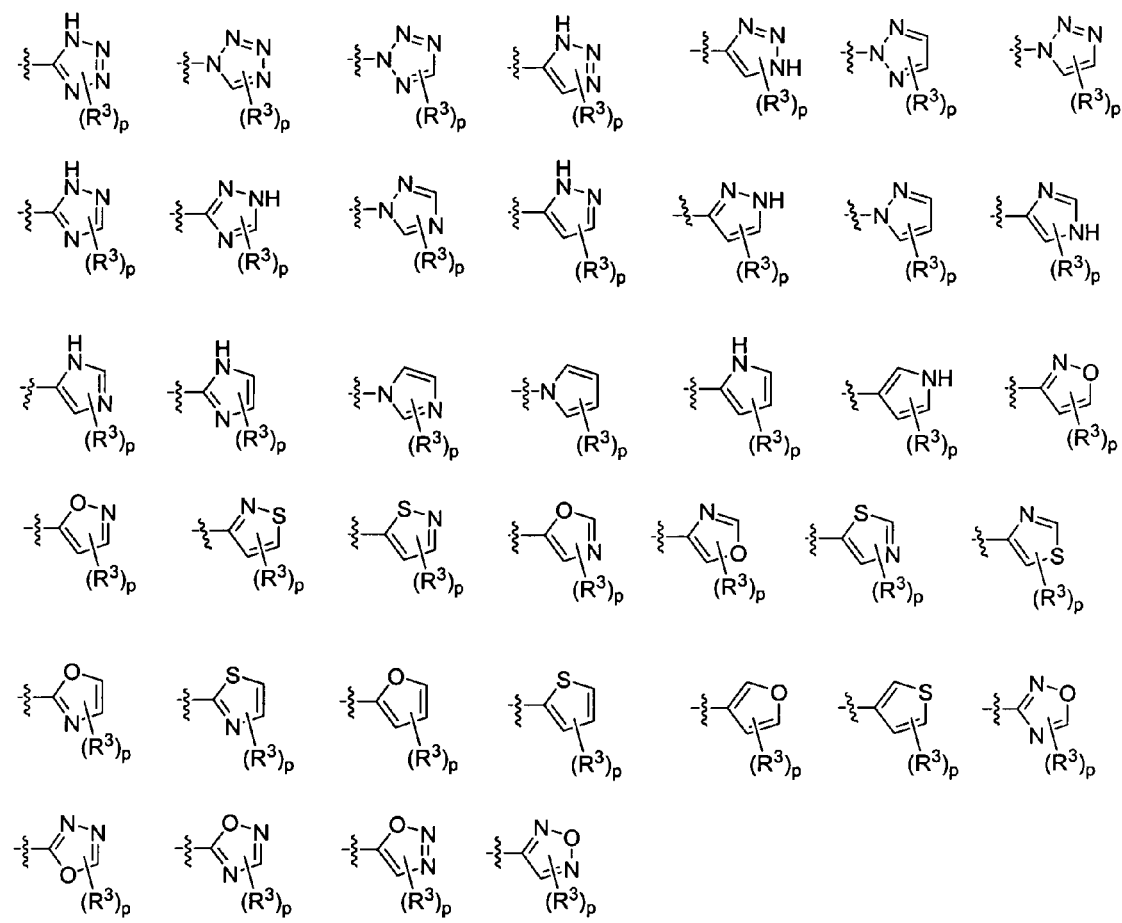
FIG. 2 shows the subformulae of certain preferred B substituents of the invention.
Figure 3:
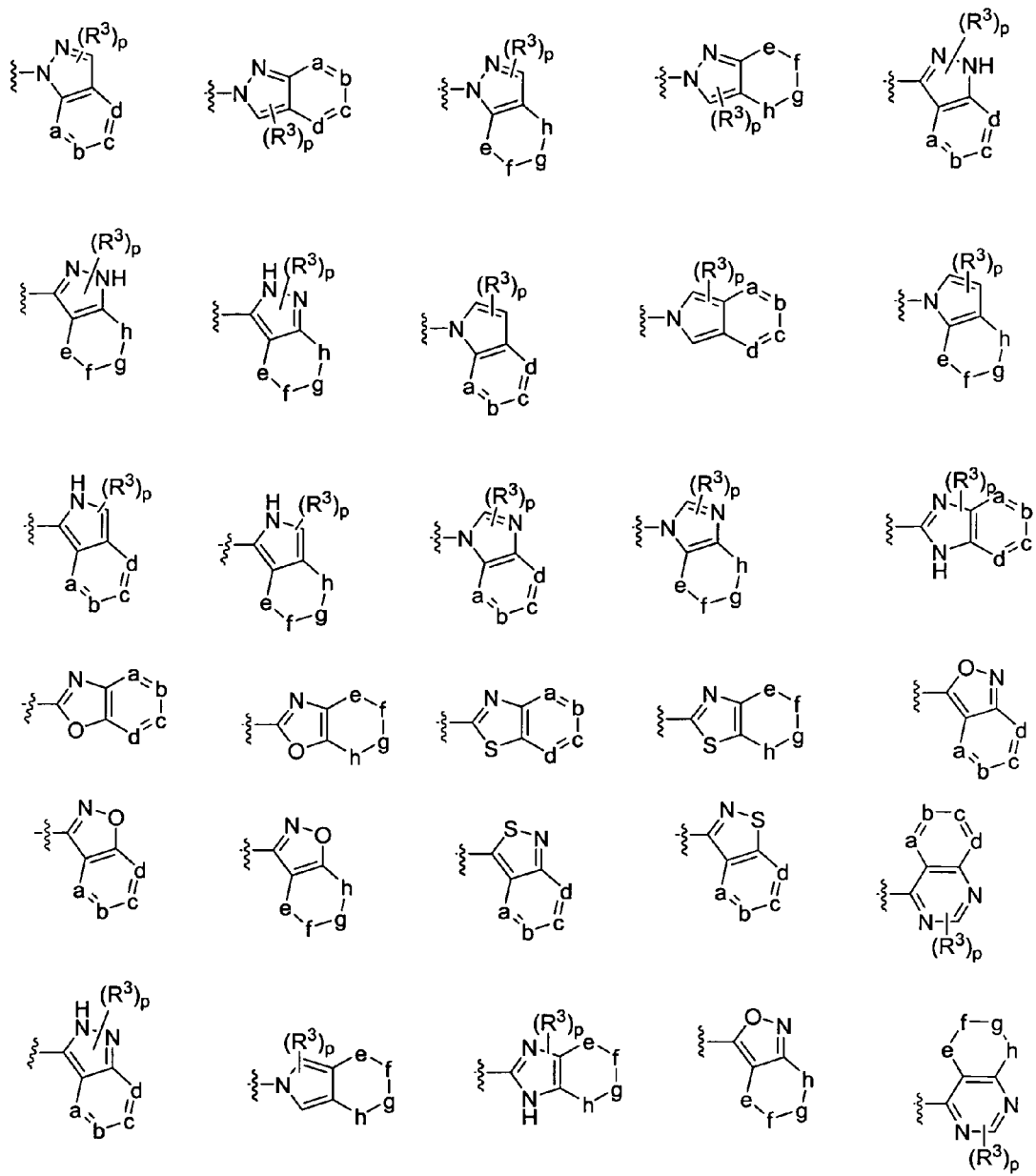
FIG. 3 shows the subformulae of certain preferred B substituents of the invention.
Figure 4:
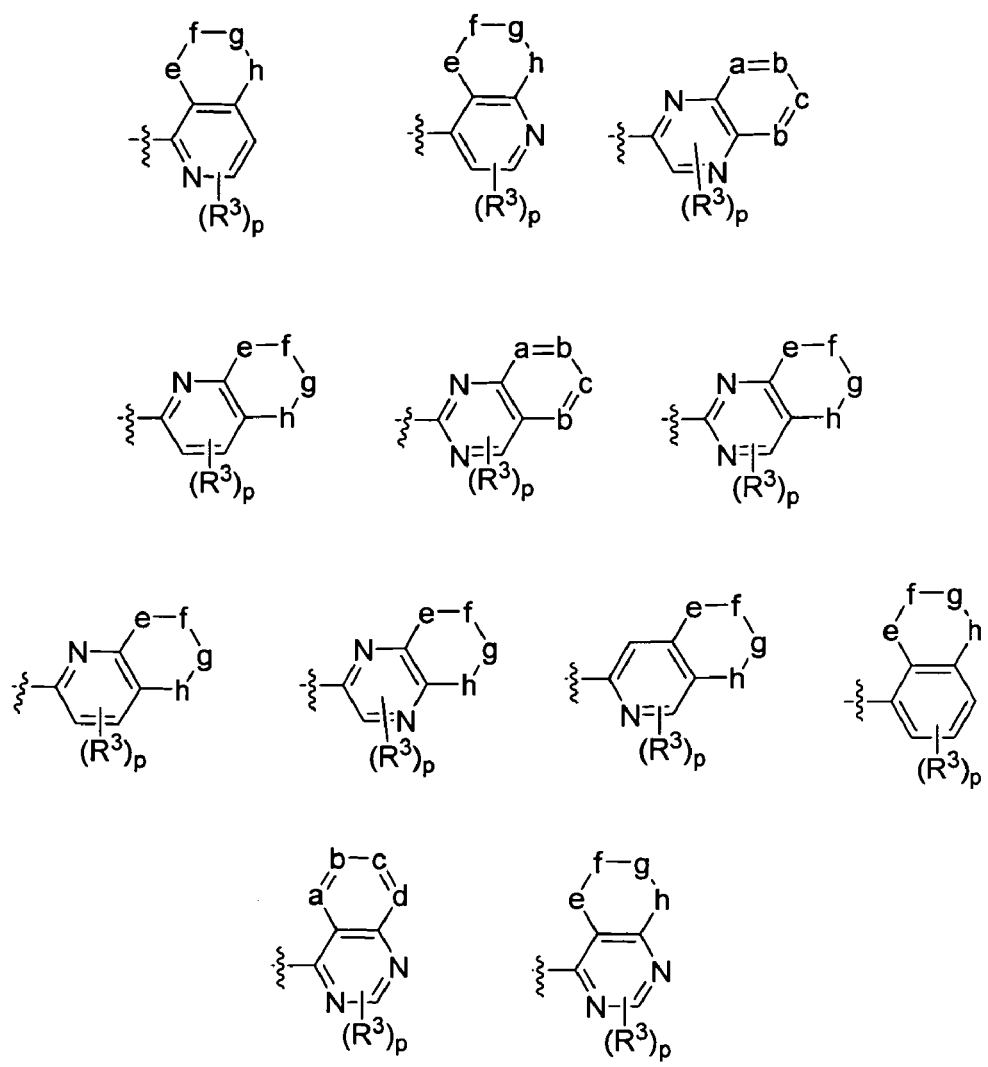
FIG. 4 shows the subformulae of certain preferred B substituents of the invention.

In yet another embodiment, the symbol B has the formula selected from the group set forth in FIG. 2, wherein the subscript p is an integer from 0-3; and wherein the $R^3$ substituent, at each occurrence is each independently selected from the group as described above for the $R^3$ substitutents for FIG. 1. In yet another embodiment, in compounds having formula I the symbol B is a bicyclic ring system having the formula selected from the group set forth in FIGS. 3 and 4, wherein the ring vertices a, b, c and d are each independently selected from the group consisting of CH, $CR^3$, N and NO; the ring vertices e, f, g and h are each independently selected from the group consisting of $CH_2$, $CHR^3$, $C(R^3)_2$, S, SO, $SO_2$, NH, $NR^3$ and O; the subscript p is an integer from 0-3; and wherein the $R^3$ substituent, at each occurrence is each independently selected from the group as described above for the $R^3$ substitutents for FIG. 1.

Still other groups of $R^3$ selections are those in which each $R^3$ is independently selected from the group consisting of hydrogen, halogen, chloro, fluoro, bromo, oxazolyl, pyridyl, pyrimidinyl, oxadiazolyl, thiazolyl, —$R^h$ or cyano. In another group of embodiments, each $R^3$ is independently selected from the group consisting of halogen, $C_{1-4}$ alkyl and $C_{1-4}$ haloalkyl, wherein the aliphatic portions are optionally substituted with from one to three members selected from the group consisting of —OH, —$OR^o$, —$OC(O)NHR^o$, —OC(O)N$(R^o)_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)NH_2$, —$C(O)NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —$NR^oCO_2R^o$, —CN, —$NO_2$, —$NH_2$, —$NHR^o$, —$N(R^o)_2$, —$NR^oS(O)NH_2$ and —$NR^oS(O)_2NHR^o$, wherein each $R^o$ is independently an unsubstituted $C_{1-6}$ alkyl.

Figure 5:
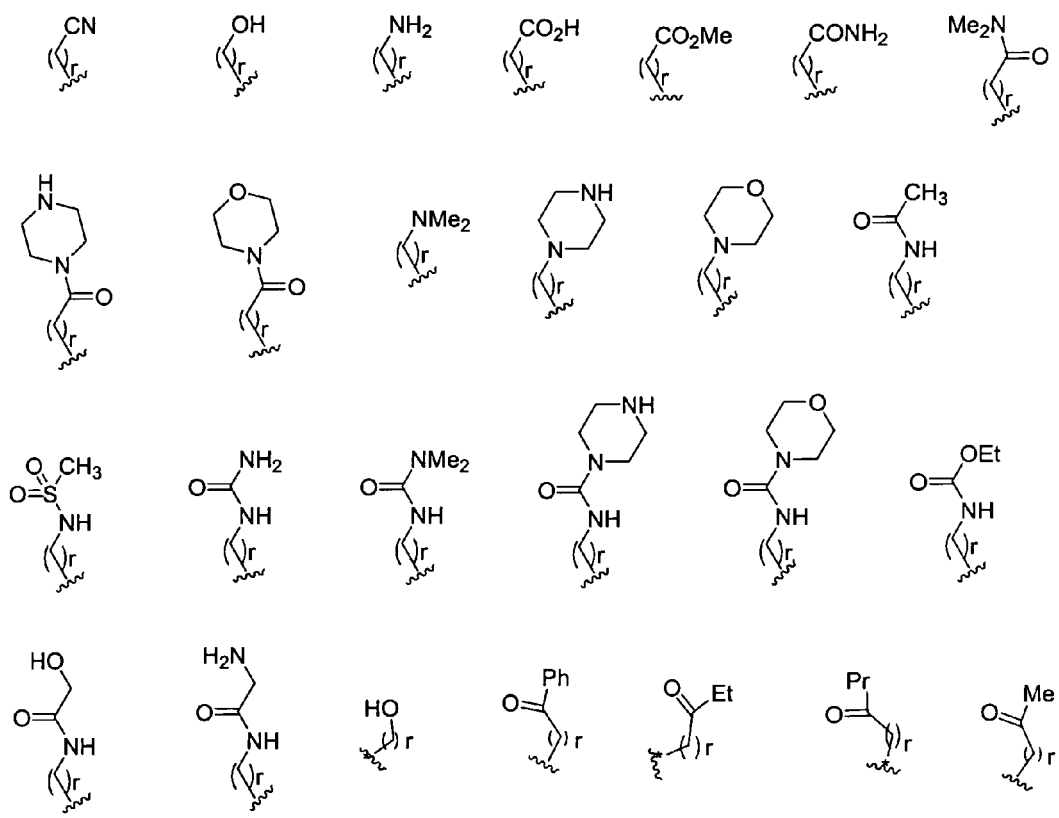
FIG. 5 shows the subformulae of certain preferred A substituents of the present invention.

The A group:

In some embodiments, the letter A in formula I represents those groups provided in FIG. 5 wherein the subscript r is an integer of from 0 to 4. In still other embodiments, A is selected from those groups in FIG. 5 in which the subscript r is an integer of from 0 to 2. In still another group of embodiments, A is selected from those groups in FIG. 5 wherein the subscript r is 0 or 1.

OTHER EMBODIMENTS

In other embodiments, compounds are provided in which: m is 0; X is —CH$_2$—; A is hydrogen or hydroxy; L$^1$ is selected from the group consisting of —CH$_2$—, —CH$_2$CH$_2$— and —CH=CH—; and B is a pyrazolyl or pyridopyrazolyl ring attached to the remainder of the molecule via a nitrogen atom ring member. Preferred R$^3$ substituents are those that have been described above. In still other embodiments, preferred, selected or identified groups in each of A, B, L$^1$, m, R$^1$, R$^{2a}$, R$^{2b}$, R$^{2c}$, R$^{2d}$, R$^{2e}$ are combined.

In another embodiment of the invention, compounds having formula I are selected from the group set forth in Table 1.

Figure 6:
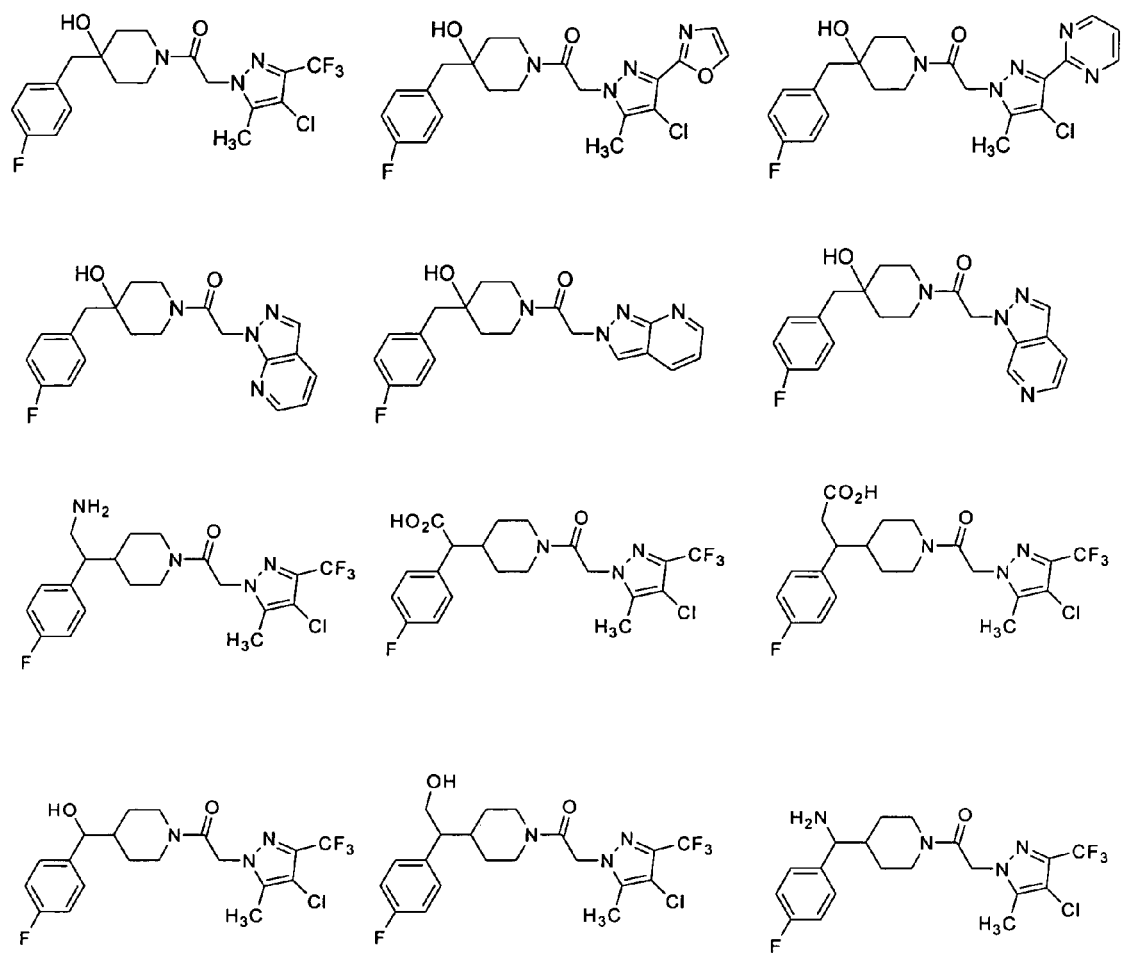
FIG. 6 shows certain piperidine derivatives of the invention.

In yet another embodiment of the invention, the compound having formula I is selected from the group set forth on FIG. 6.

Figure 7:
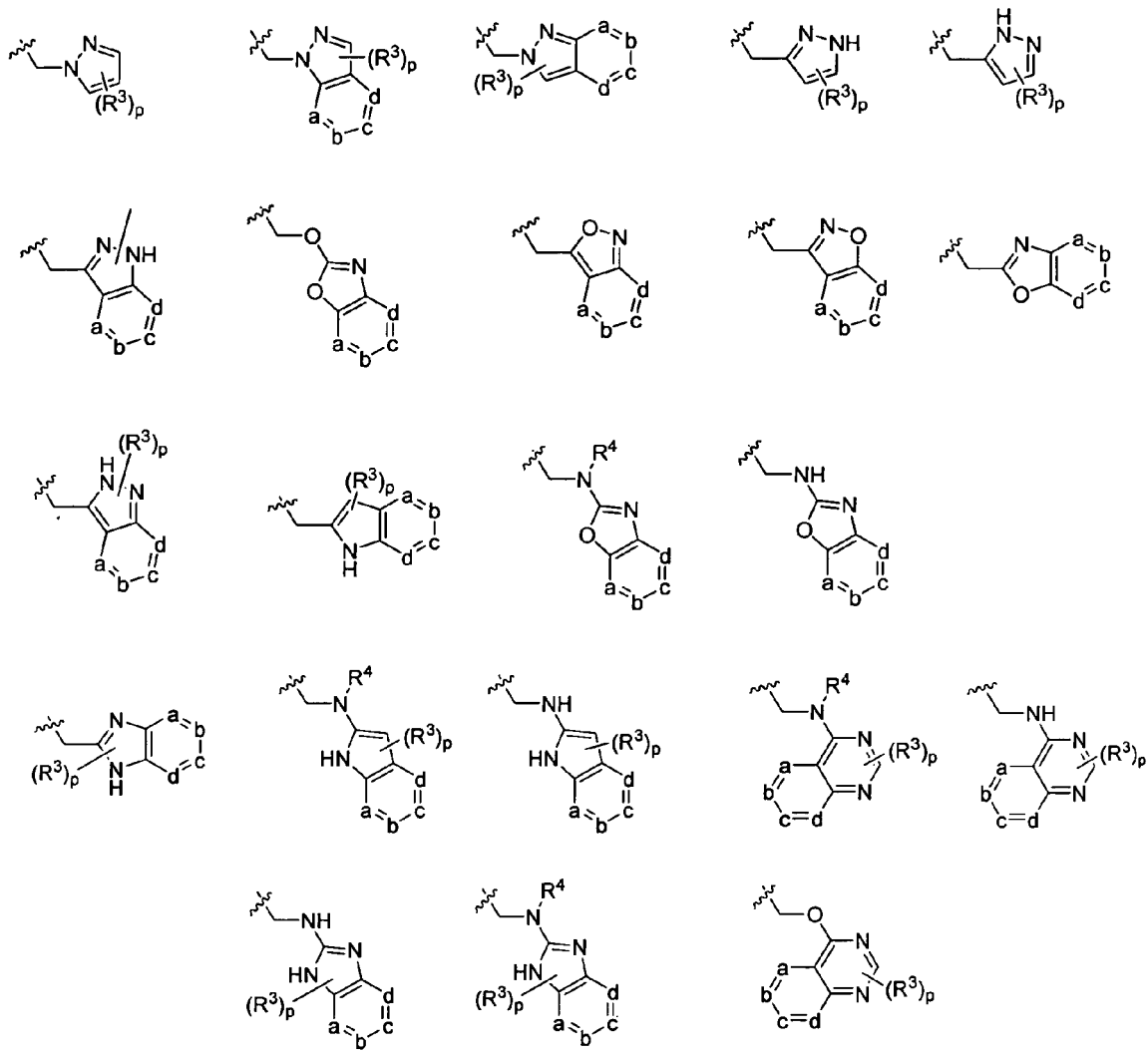
FIG. 7 shows the subformulae of certain preferred —$L^1$—B groups of the invention.

The —L$^1$—B Group:

In certain embodiments, —L$^1$—B has a formula as set forth on FIG. 7. In FIG. 7, the ring vertices a, b, c and d are each independently CH, C(R$^3$), N or NO; and at each occurrence, R$^3$ is selected from the substituents provided above with reference to B.

Preparation of Compounds

As shown in the examples below, there are variety of synthetic routes by which a skilled artisan can prepare compounds and intermediates of the present invention. Schemes 1A-1I illustrate several methods for the preparation of certain piperidine derivatives of the invention or their intermediates. In each of these schemes, P is a protecting group, X is a leaving group, such as a halogen atom; Nu is a nucleophile, and non-interfering substituents are provided as —R, —R', —R", and —R'".

The schemes below provide certain synthetic routes that can be followed to access certain piperidine derivative of the invention. Other routes or modification of the routes presented below would be readily apparent to a skilled artisan and within the scope of the present invention.

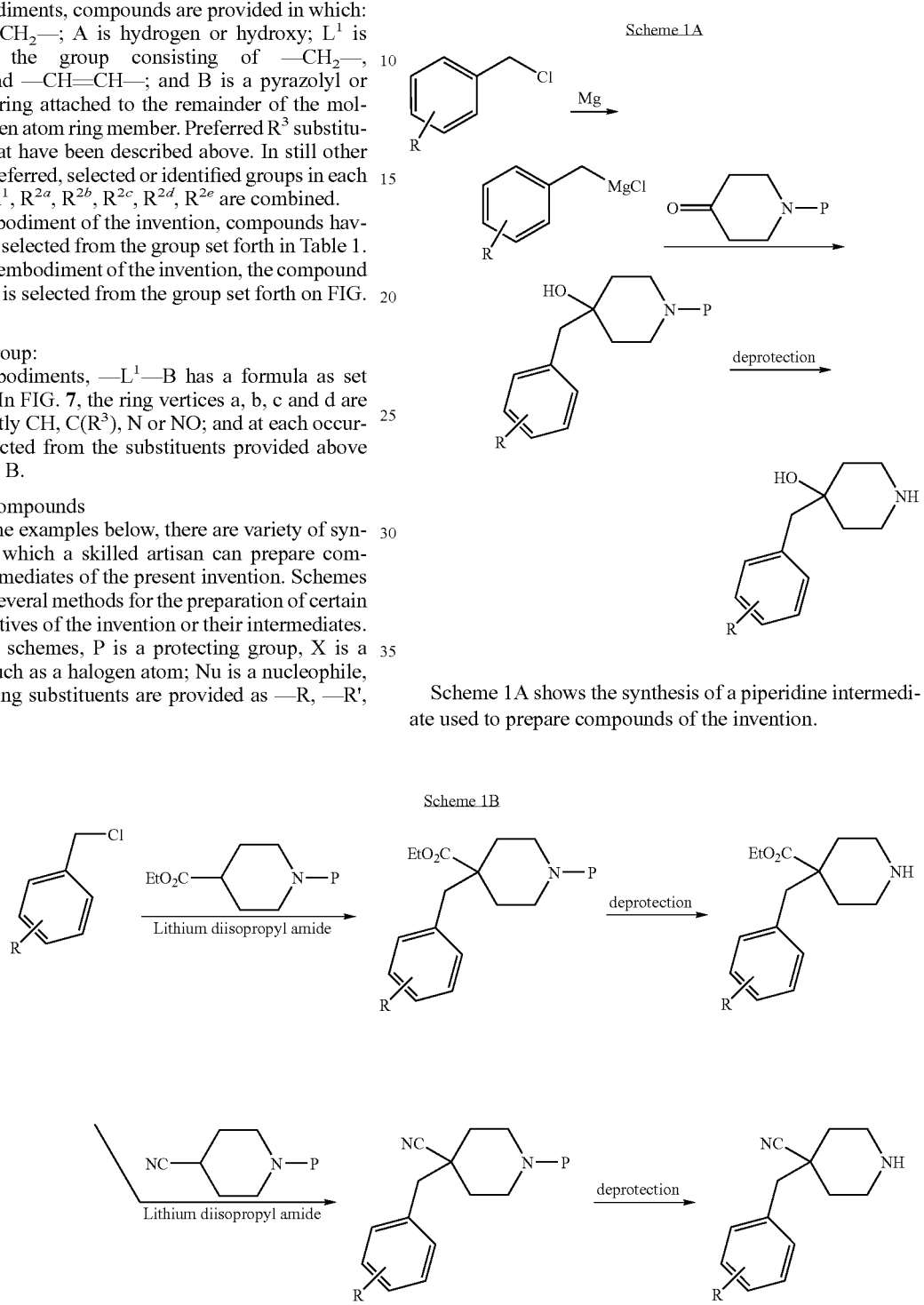

Scheme 1A shows the synthesis of a piperidine intermediate used to prepare compounds of the invention.

Scheme 1B shows the syntheses of certain piperidine intermediates used to prepare compound of the invention.
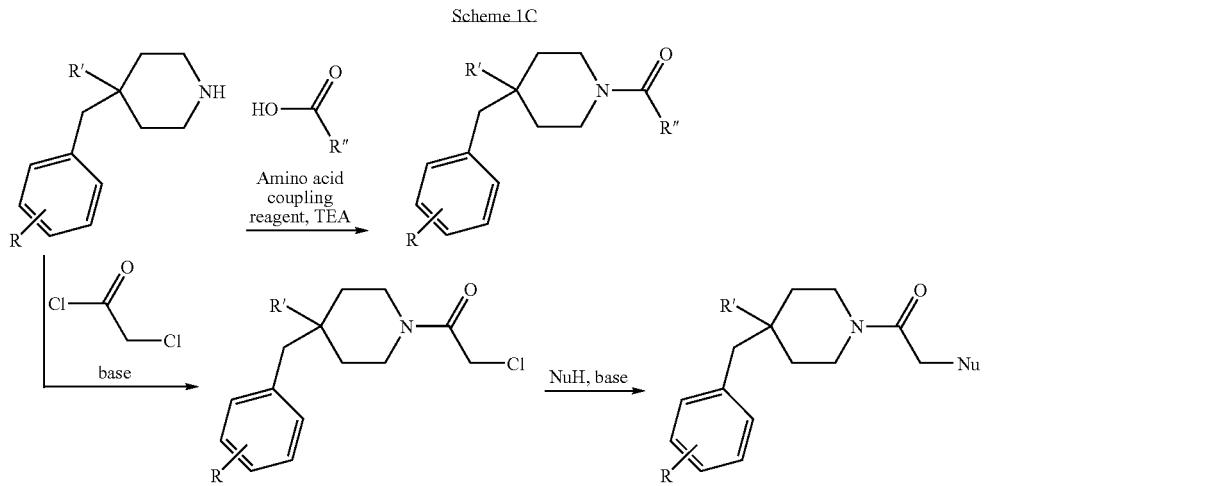
Scheme 1C shows the synthesis of certain piperidine derivatives of the present invention.
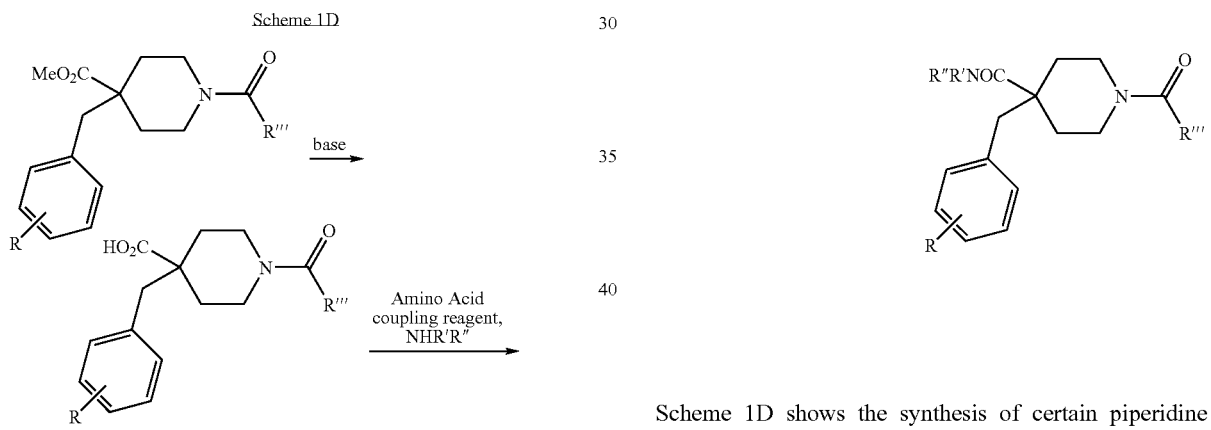
Scheme 1D shows the synthesis of certain piperidine derivatives of the present invention.
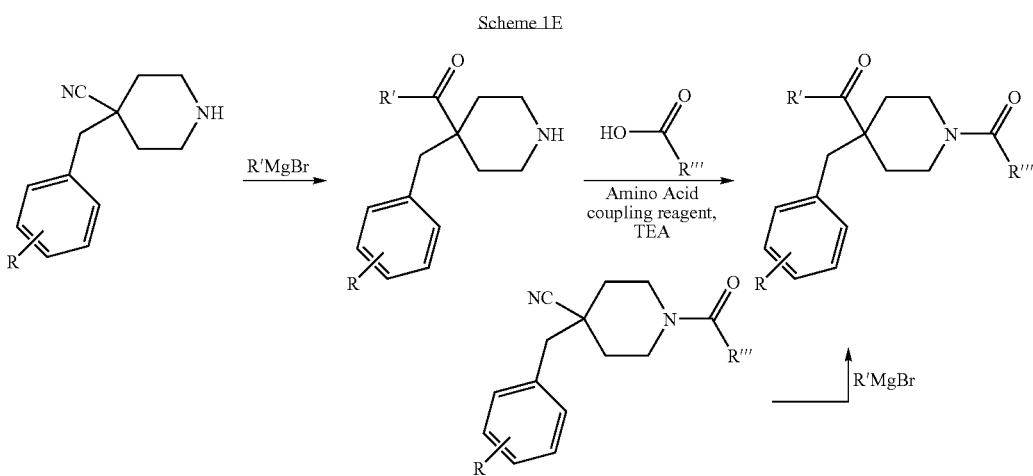

Scheme 1E shows the synthesis of certain piperidine derivatives of the present invention.

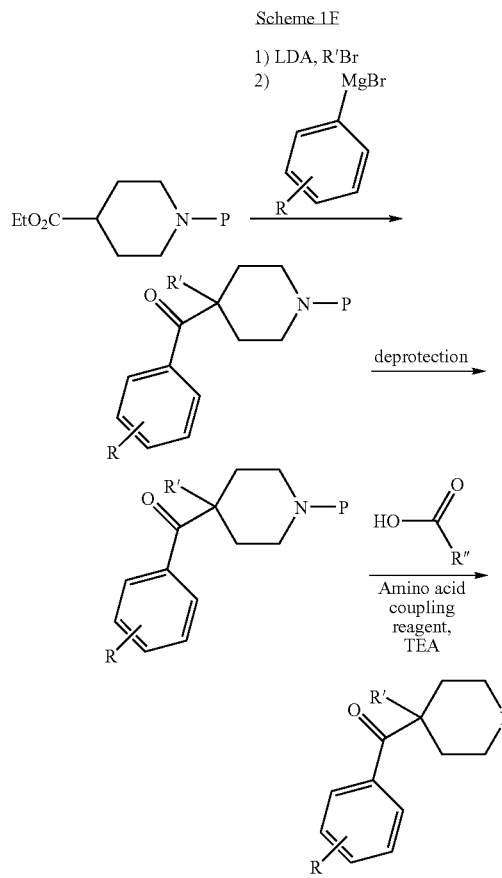

Scheme 1F shows the synthesis of certain piperidine derivatives of the present invention.

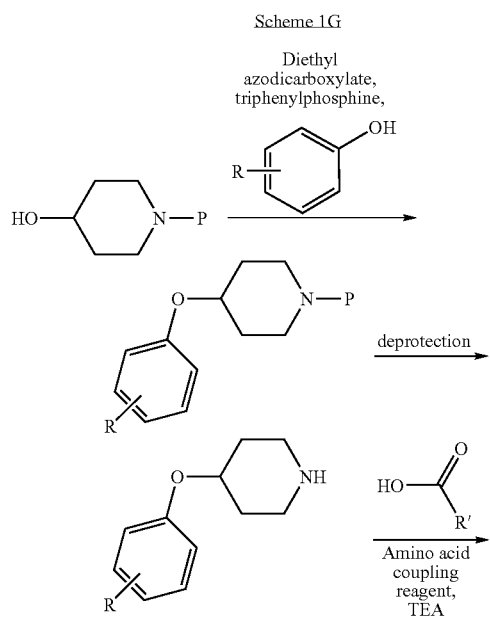

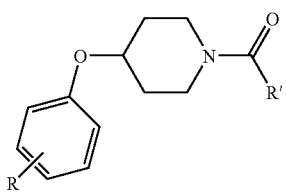

Scheme 1G shows the synthesis of certain piperidine derivatives of the present invention.

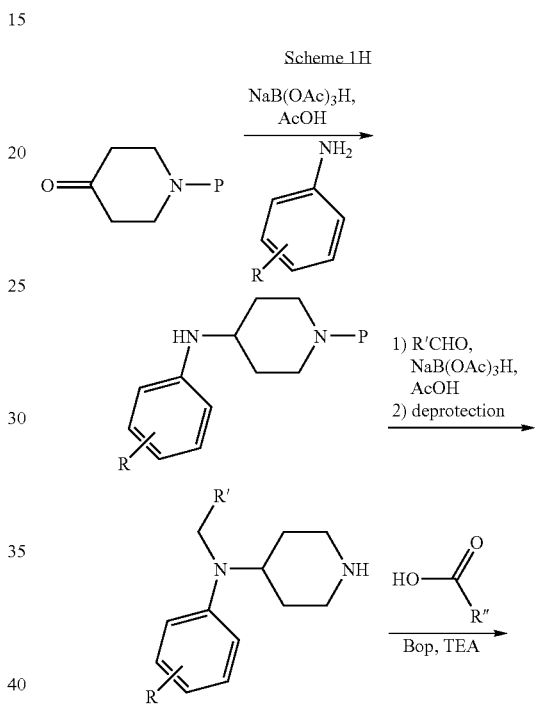

Scheme 1H shows the synthesis of certain piperidine derivatives of the present invention.

A family of specific compounds of particular interest having formula I consists of compounds, pharmaceutically acceptable salts, hydrates or N-oxides thereof, as set forth in Table 1.

TABLE 1

1. 2-(4-Chloro-5-methyl-3-trifluoromethyl-pyrazol-1-yl)-1-[4-(4-fluoro-benzyl)-4-hydroxy-piperidin-1-yl]-ethanone
2. 2-(4-Chloro-5-methyl-3-oxazol-2-yl-pyrazol-1-yl)-1-[4-(4-fluoro-benzyl)-4-hydroxy-piperidin-1-yl]-ethanone
3. 6-Chloro-3-{2-[4-(4-fluoro-benzyl)-4-hydroxy-piperidin-1-yl]-2-oxo-ethyl}-3H-benzooxazol-2-one

IV. Pharmaceutical Compositions

In addition to having a compound(s) of formula I provided above, the compositions for modulating CCR1, CCR2 and CCR3 activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Pat. No. 6,451,339, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-Occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of the invention may be formulated for depositing into a medical device, which may include any of a variety of conventional grafts, stents, including stent grafts, catheters, balloons, baskets or other device that can be deployed or permanently implanted within a body lumen. As a particular example, it would be desirable to have devices and methods which can deliver compounds of the invention to the region of a body which has been treated by interventional technique.

In exemplary embodiment, the inhibitory agent of this invention may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No. 4,886,062 (Wiktor). Such designs include both metal and polymeric stents, as well as self-expanding and balloon-expandable stents. Stents may also used to deliver a drug at the site of contact with the vasculature, as disclosed in U.S. Pat. No. 5,102,417 (Palmaz) and in International Patent Application Nos. WO 91/12779 (Medtronic, Inc.) and WO 90/13332 (Cedars-Sanai Medical Center), U.S. Pat. No. 5,419,760 (Narciso, Jr.) and U.S. Pat. No. 5,429,634 (Narciso, Jr.), for example. Stents have also been used to deliver viruses to the wall of a lumen for gene delivery, as disclosed in U.S. patent application Ser. No. 08/746,404, filed Nov. 8, 1996 (Donovan et al.).

The term "deposited" means that the inhibitory agent is coated, adsorbed, placed, or otherwise incorporated into the device by methods known in the art. For example, the inhibitory agent may be embedded and released from within ("matrix type") or surrounded by and released through ("reservoir type") polymer materials that coat or span the medical device. In the later example, the inhibitory agent may be entrapped within the polymer materials or coupled to the polymer materials using one or more the techniques for generating such materials known in the art. In other formulations, the inhibitory agent may be linked to the surface of the medical device without the need for a coating by means of detachable bonds and release with time, can be removed by active mechanical or chemical processes, or are in a permanently immobilized form that presents the inhibitory agent at the implantation site.

In one embodiment, the inhibitory agent may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly (lactide-co-glycolide) (PLLA/PGA), poly(hydroxybutyrate), poly(hydroxybutyrate-co-valerate), polydioxanone, poly-orthoester, polyanhydride, poly(glycolic acid), poly(D-lactic acid), poly(L-lactic acid), poly(D,L-lactic acid), poly(D,L-lactide) (PLA), poly (L-lactide) (PLLA), poly(glycolic acid-co-trimethylene carbonate) (PGA/PTMC), polyethylene oxide (PEO), polydioxanone (PDS), polyphosphoester, polyphosphoester urethane, poly(amino acids), cyanoacrylates, poly(trimethylene carbonate), poly(iminocarbonate), copoly (ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable poplymers known in the art. Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In one embodiment of the invention, the inhibitory agent of the invention is coupled to a polymer or semipermeable polymer matrix that is formed as a stent or stent-graft device.

Typically, polymers are applied to the surface of an implantable device by spin coating, dipping or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In preferred embodiments of the invention, the inhibitory agent is formulated for release from the polymer coating into the environment in which the medical device is placed. Preferably, the inhibitory agent is released in a controlled manner over an extended time frame (e.g., months) using at least one of several well-known techniques involving polymer carriers or layers to control elution. Some of these techniques were previously described in U.S. Patent Application 20040243225A1, the entire disclosure of which is incorporated in its entirety.

Moreover, as described for example in U.S. Pat. No. 6,770,729, which is incorporated herein in its entirety, the reagents and reaction conditions of the polymer compositions can be manipulated so that the release of the inhibitory agent from the polymer coating can be controlled. For example, the diffusion coefficient of the one or more polymer coatings can be modulated to control the release of the inhibitory agent from the polymer coating. In a variation on this theme, the diffusion coefficient of the one or more polymer coatings can be controlled to modulate the ability of an analyte that is present in the environment in which the medical device is placed (e.g. an analyte that facilitates the breakdown or hydrolysis of some portion of the polymer) to access one or more components within the polymer composition (and for example, thereby modulate the release of the inhibitory agent from the polymer coating). Yet another embodiment of the invention includes a device having a plurality of polymer coatings, each having a plurality of diffusion coefficients. In such embodiments of the invention, the release of the inhibitory agent from the polymer coating can be modulated by the plurality of polymer coatings.

In yet another embodiment of the invention, the release of the inhibitory agent from the polymer coating is controlled by modulating one or more of the properties of the polymer composition, such as the presence of one or more endogenous or exogenous compounds, or alternatively, the pH of the polymer composition. For example, certain polymer compositions can be designed to release a inhibitory agent in response to a decrease in the pH of the polymer composition. Alternatively, certain polymer compositions can be designed to release the inhibitory agent in response to the presence of hydrogen peroxide.

V. Methods of Treating Diseases Modulated by CCR1, CCR2 and/or CCR3

In yet another aspect, the present invention provides methods of treating CCR1-, CCR2- and/or CCR3-mediated conditions or diseases by administering to a subject having such a disease or condition, a therapeutically effective amount of a compound of formula I above. The "subject" is defined herein to include animals such as mammals, including, but not limited to, primates (e.g., humans), cows, sheep, goats, horses, dogs, cats, rabbits, rats, mice and the like.

CCR1 provides a target for interfering with or promoting specific aspects of immune cell functions, or more generally, with functions associated with CCR1 expression on a wide range of cell types in a mammal, such as a human. Compounds that inhibit CCR1, are particularly useful for modulating monocyte, macrophage, lymphocyte, granulocyte, NK cell, mast cells, dendritic cell, and certain immune derived cell (for example, osteoclasts) function for therapeutic purposes. Accordingly, the present invention is directed to compounds which are useful in the prevention and/or treatment of a wide variety of inflammatory and immunoregulatory disorders and diseases (see Saeki, et al., *Current Pharmaceutical Design* 9:1201-1208 (2003)).

For example, an instant compound that inhibits one or more functions of CCR1 may be administered to inhibit (i.e., reduce or prevent) inflammation or cellular infiltration associated with an immune disorder. As a result, one or more inflammatory processes, such as leukocyte emigration or infiltration, chemotaxis, exocytosis (e.g., of enzymes, histamine) or inflammatory mediator release, can be inhibited. For example, monocyte infiltration to an inflammatory site (e.g., an affected joint in arthritis, or into the CNS in MS) can be inhibited according to the present method.

Similarly, an instant compound that promotes one or more functions of CCR1 is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, monocytes can be recruited to combat bacterial infections.

Diseases and conditions associated with inflammation, immune disorders and infection can be treated using the method of the present invention. In a preferred embodiment, the disease or condition is one in which the actions of immune cells such monocyte, macrophage, lymphocyte, granulocyte, NK cell, mast cell, dendritic cell, or certain immune derived cell (for example, osteoclasts) are to be inhibited or promoted, in order to modulate the inflammatory or autoimmune response.

In one group of embodiments, diseases or conditions, including chronic diseases, of humans or other species can treated with modulators of CCR1, CCR2 or CCR3 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as asthma, allergic asthma, allergic rhinitis, hypersensitivity lung diseases and the like, (9) autoimmune diseases, such as fibromyalagia, scleroderma, ankylosing spondylitis, juvenile RA, Still's disease, polyarticular juvenile RA, pauciarticular juvenile RA, polymyalgia rheumatica, Takuyasu arthritis, rheumatoid arthritis, psoriatic arthritis, osteoarthritis, polyarticular arthritis, multiple sclerosis, systemic lupus erythematosus, type I diabetes, type II diabetes, type I diabetes (recent onset), optic neuritis, glomerulonephritis, and the like, (10) graft rejection including allograft rejection and acute and chronic graft-vs-host disease, (11) fibrosis (e.g. pulmonary fibrosis (i.e. idiopathic pulmonary fibrosis, interstitial pulmonary fibrosis), fibrosis associated with end-stage renal disease, fibrosis caused by radiation, tubulointerstitial fibrosis, subepithelieal fibrosis, scleroderma (progressive systemic sclerosis), hepatic fibrosis (including that caused by alcoholic or viral hepatitis), primary and secondary cirrhosis), (12) acute and chronic lung inflammation (chronic obstructive pulmonary disease, chronic bronchitis, adult respiratory distress syndrome, respiratory distress syndrome of infancy, immune complex alveolitis) and (13) other diseases in which undesired inflammatory responses or immune disorders are to be inhibited, such as cardiovascular disease including atherosclerosis, vascular inflammation resulting from tissue transplant or during restenosis (including, but not limited to restenosis following angioplasty and/or stent insertion), other acute and chronic inflammatory conditions such as myositis, neurodegenerative diseases (e.g., Alzheimer's disease), encephalitis, meningitis, hepatitis, nephritis, sepsis, sarcoidosis, allergic conjunctivitis, otitis, sinusitis, synovial inflammation caused by arthroscopy, hyperuremia, trauma, ischaemia reperfusion injury, nasal polyosis, preeclampsia, oral lichen planus, Guillina-Barre syndrome, granulomatous diseases, conditions associated with leptin production, Behcet's syndrome and gout and in wound healing applications (14) immune mediated food allergies such as Celiac disease.

In another group of embodiments, diseases or conditions can be treated with modulators of CCR1 function. Examples of diseases to be treated with modulators of CCR1 function include cancers (both primary and metastatic) (e.g., multiple myeloma; Hata, H., Leukemia & Lymphoma, 2005, 46(7); 967-972), cardiovascular diseases, diseases in which angiogenesis or neovascularization play a role (neoplastic diseases, retinopathy and macular degeneration), infectious diseases (viral infections, e.g., HIV infection, and bacterial infections) and immunosuppressive diseases such as organ transplant conditions and skin transplant conditions. The term "organ transplant conditions" is meant to include bone marrow transplant conditions and solid organ (e.g., kidney, liver, lung, heart, pancreas or combination thereof) transplant conditions.

Pharmaceutical compositions of this invention can also inhibit the production of metalloproteinases and cytokines at inflammatory sites, either directly or indirectly (as a consequence of decreasing cell infiltration) thus providing benefit for diseases or conditions linked to these cytokines.

The compounds of the present invention are accordingly useful in the prevention and treatment of a wide variety of inflammatory and immunoregulatory disorders and diseases.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

Diseases and conditions associated with inflammation, immune disorder, infection and cancer can be treated or prevented with the present compounds, compositions, and methods.

The compounds and compositions of the present invention can be combined with other compounds and compositions having related utilities to prevent and treat the condition or disease of interest, such as inflammatory or autoimmune disorders, conditions and diseases, including inflammatory bowel disease, rheumatoid arthritis, osteoarthritis, psoriatic arthritis, polyarticular arthritis, multiple sclerosis, allergic diseases, psoriasis, atopic dermatitis and asthma, and those pathologies noted above.

For example, in the treatment or prevention of inflammation or autoimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non sedating antihistamine.

Likewise, compounds and compositions of the present invention may be used in combination with other drugs that are used in the treatment, prevention, suppression or amelioration of the diseases or conditions for which compounds and compositions of the present invention are useful. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106,203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbrel®), (k) antibody therapies such as orthoclone (OKT3), daclizumab (Zenapax®), basiliximab (Simulect®) and infliximab (Remicade®), (l) other antagonists of the chemokine receptors, especially CCR5, CXCR2, CXCR3, CCR2, CCR3, CCR4, CCR7, $CX_3CR1$ and CXCR6; (m) lubricants or emollients such as petrolatum and lanolin, (n) keratolytic agents (e.g., tazarotene), (o) vitamin $D_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon (β-1α (Avonex®), azathioprine (Imurek®, Imuran®), glatiramer acetate (Capoxone®), a glucocorticoid (e.g., prednisolone) and cyclophosphamide (t) DMARDS such as methotrexate (u) other compounds such as 5-aminosalicylic acid and prodrugs thereof; hydroxychloroquine; D-penicillamine; antimetabolites such as azathioprine, 6-mercaptopurine and methotrexate; DNA synthesis inhibitors such as hydroxyurea and microtubule disrupters such as colchicine. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

VI. EXAMPLES

The following examples are offered to illustrate, but not to limit the claimed invention.

Reagents and solvents used below can be obtained from commercial sources such as Aldrich Chemical Co. (Milwaukee, Wis., USA). $^1$H-NMR were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In tables, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC equipped with an Agilent Zorbax SB-C18, 2.1×50 mm, 5μ column for sample delivery. Normally the analyte was dissolved in methanol at 0.1 mg/mL and 1 microlitre was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM $NH_4OAc$ in acetonitrile/water as delivery system.

The following abbreviations are used in the Examples and throughout the description of the invention: NMP, N-methyl-2-pyrrolidinone; HPLC, High Pressure Liquid Chromatography; DMF, Dimethyl formamide; TFA, Trifluoroacetic Acid; THF, Tetrahydrofuran; NCS, N-CHlorosuccinimide; EtOAc, Ethyl acetate; $BOC_2O$, di-tertbutyl dicarbonate or BOC anhydride; TEA, Triethylamine; BOP, O-Benzotriazol-1-yloxytris (dimethylamino)phosphonium hexafluorophosphate; PyBOP, (Benzotriazol-1-yloxy)tripyrrolidino-phosphonium Hexafluorophosphate; HATU, O-(7-Azabenzotriazol-1-yl)-1,1,3,3-tetramethyluronium hexafluorophosphate; rt, room temperature; LDA, Lithium diisopropyl amide; DIPEA, Diisopropyl ethylamine; DMA, Dimethylacetamide.

Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them.

Two regioisomers can sometimes exist for certain compounds of the invention. For these cases, both regioisomeric types have demonstrated biological properties and are meant to be within the scope of all the appended claims, whether explicitly drawn or not.

31

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1

2-(4-Chloro-5-methyl-3-(2-oxazolyl)-pyrazol-1-yl)-1-[4-(4-fluoro-benzyl)-4-hydroxy-piperidin-1-yl]-ethanone

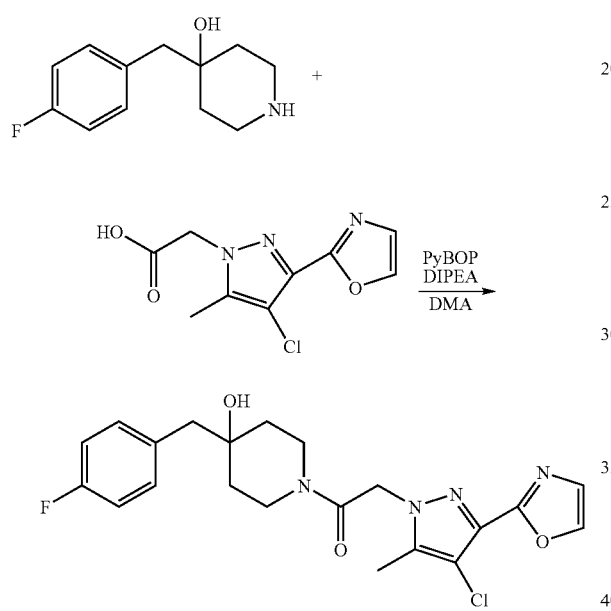

To a 20 mL vial equipped with a magnetic stirring bar was added 63 mg of 4-(4-Fluoro-benzyl)-piperidin-4-ol (0.3 mmol, 1.2 equiv.), 62 mg of (4-Chloro-5-methyl-3-oxazol-2-yl-pyrazol-1-yl)-acetic acid (0.26 mmol, 1.0 equiv), and 138 mg of benzotriazol-1-yloxy)tripyrrolidinophosphonium hexafluorophosphate (0.27 mmol, 1.0 equiv). The reagents were dissolved in 0.6 mL of DMA and to the resultant solution was added 0.18 mL of DIPEA (1.0 mmol, 3.8 equiv.). The reaction solution was stirred for 14 h and then poured into 50 mL of EtOAc. The organic extracts were washed with saturated aq. NaCl (5×10 mL), 1% aq NaOH (1×10 mL), and 0.1 N HCl (1×10 mL). The organic extracts were dried over MgSO$_4$ and concentrated in vacuo to afford a yellow oil, which was purified by preparative HPLC to afford 34 mg of 2-(4-Chloro-5-methyl-3-oxazol-2-yl-pyrazol-1-yl)-1-[4-(4-fluoro-benzyl)-4-hydroxy-piperidin-1-yl]-ethanone (30% yield): MS (ES) M+H expected=413.2, found 413.2. $^1$H NMR (CDCl$_3$, 400 MHz, 23° C.) δ 7.69 (s, 1H), 7.27 (s, 1H), 7.11-7.14 (m, 2H), 6.98-7.03 (m, 2H), 5.06 (d, J=16.0 Hz, 1H), 4.93 (d, J=16.0 Hz, 1H), 4.32-4.35 (m, 1H), 3.66-3.69 (m, 1H), 3.43-3.50 (m, 1H), 2.96-3.03 (m, 1H), 2.74 (s, 2H), 2.30 (s, 3H), 1.55-1.63 (m, 4H).

Example 2

Synthesis of 3-(4-Chloro-5-methyl-3-trifluoromethyl-pyrazol-1-yl)-1-[4-(4-fluoro-benzyl)-4-hydroxy-piperidin-1-yl]-propan-1-one

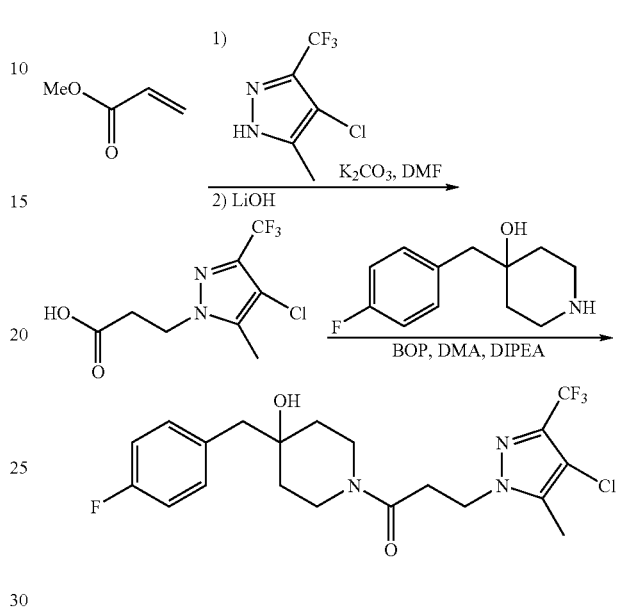

The title compound was prepared according to the procedure described in scheme above. LCMS observed for (M+H)$^+$: 448.2

Example 3

(E) and (Z) 3-(4-Chloro-5-methyl-3-trifluoromethylpyrazol-1-yl)-acrylic acid

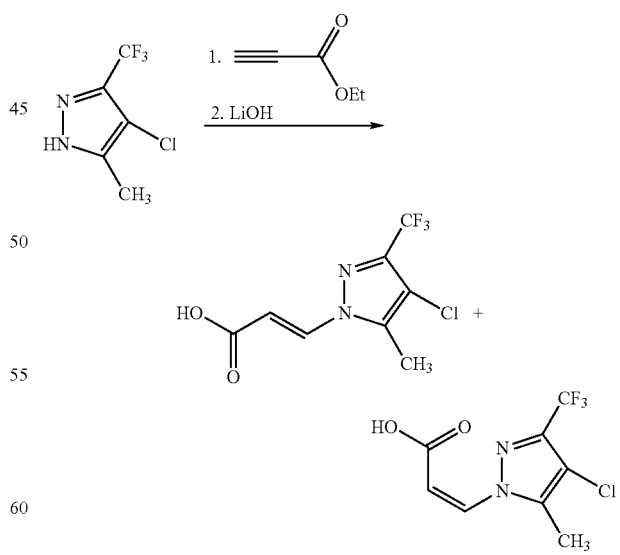

To a vial containing 4-Chloro-5-methyl-3-trifluoromethyl-1H-pyrazole (2.83 g, 15.3 mmol) was added MeOH (5 mL) and ethyl propiolate (1.94 g, 19.7 mmol) and acetic acid (100 µL). The vial was capped and the reaction mixture was heated to 80° C. for 20 h. After cooling to room temperature, the volatiles were removed in vacuo to afford the crude products, which were purified by flash chromatography on silica gel (120 g) using gradient elution (0%-75% EtOAc in hexanes over 15 column volumes). The fractions containing the E and Z esters were collected separately and concentrated in vacuo. Each product was then transferred to a separate vial using THF (10 mL). Both vials were treated with a 1.0 N solution of LiOH (10 mL). The vials were heated to 40° C. After 2 h, the solutions were cooled, and each was diluted with water (50 mL). The pH was adjusted to 1 with 4 N HCl. Each aqueous phase was extracted with EtOAc (2×25 mL). The organic phases were dried over MgSO$_4$ and concentrated in vacuo to afford (E)-3-(4-Chloro-5-methyl-3-trifluoromethylpyrazol-1-yl)-acrylic acid (2.21 g, 57% yield) HPLC retention time=2.18 minutes. MS (ES) [M−H]$^−$ expected 253.0, found 252.9; and (Z)-3-(4-Chloro-5-methyl-3-trifluoromethylpyrazol-1-yl)acrylic acid (749 mg, 19% yield). MS (ES) [M−H]$^−$ expected 253.0, found 252.9.

Example 4

(E)-1-(4-(4-fluorobenzyl)-4-hydroxypiperidin-1-yl)-3-(4-Chloro-3-(trifluoromethyl)-5-methyl-1H-pyrazol-1-yl)prop-2-en-1-one

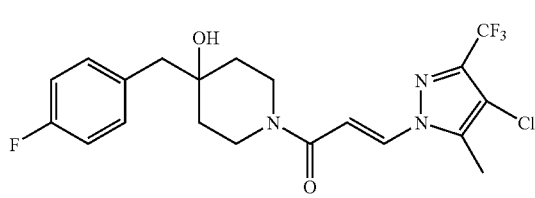

The title compound was prepared according to the procedure described in EXAMPLE 1 using (E)-3-(4-Chloro-5-methyl-3-trifluoromethylpyrazol-1-yl)-acrylic acid. MS (ES) [M+H]$^+$ expected 446.1, found 446.1.

Example 5

(Z)-1-(4-(4-fluorobenzyl)-4-hydroxypiperidin-1-yl)-3-(4-Chloro-3-(trifluoromethyl)-5-methyl-1H-pyrazol-1-yl)prop-2-en-1-one

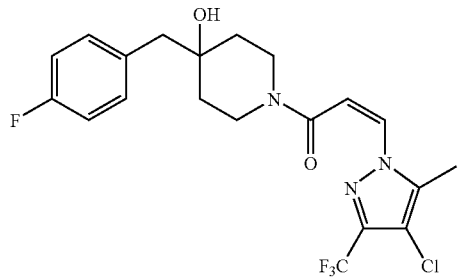

The title compound was prepared according to the procedure described in EXAMPLE 1 using (Z)-3-(4-Chloro-5-methyl-3-trifluoromethylpyrazol-1-yl)-acrylic acid. MS (ES) [M+H]$^+$ expected 446.1, found 446.1.

Example 6

2-(4-Chloro-5-methyl-3-trifluoromethyl-pyrazol-1-yl)-1-[4-(4-fluoro-benzyl)-4-hydroxy-piperidin-1-yl]-ethanone

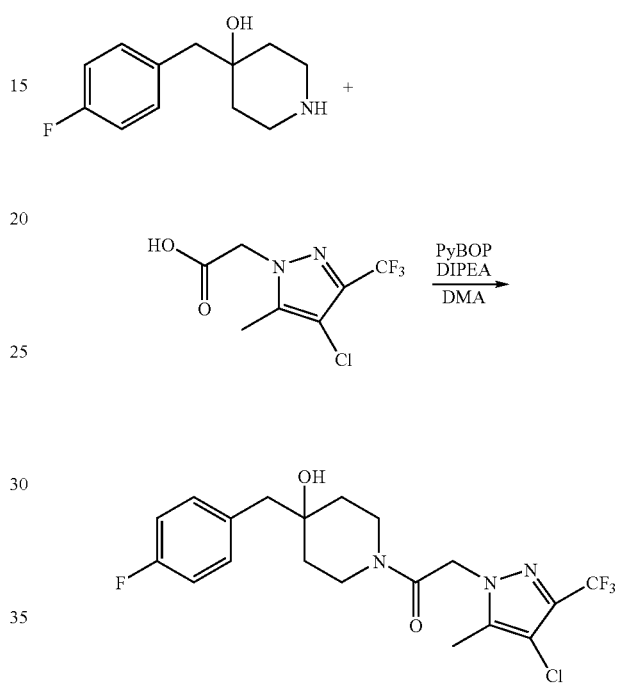

To a 20 mL vial equipped with a magnetic stirring bar was added 78 mg of 4-(4-Fluoro-benzyl)-piperidin-4-ol (0.37 mmol, 1.0 equiv.), 100 mg of (4-Chloro-5-methyl-3-trifluoromethyl-pyrazol-1-yl)-acetic acid (0.41 mmol, 1.1 equiv), and 207 mg of (Benzotriazol-1-yloxy)tripyrrolidinophosphonium hexafluorophosphate (0.40 mmol, 1.1 equiv.). The reagents were dissolved in 3 mL of DMA and to the resultant solution was added 0.26 mL of DIPEA (1.5 mmol, 4.1 equiv). The reaction solution was stirred for 5 h and then poured into 50 mL of EtOAc. The organic phase was washed with saturated aq. NaCl (5×10 mL), 1% aq NaOH (1×10 mL), and 0.1 N HCl (1×10 mL). The organic phase was then dried over MgSO$_4$ and concentrated in vacuo to afford a yellow oil, which was purified by preparative HPLC to afford 129 mg of 2-(4-Chloro-5-methyl-3-trifluoromethyl-pyrazol-1-yl)-1-[4-(4-fluoro-benzyl)-4-hydroxy-piperidin-1-yl]-ethanone (80% yield): MS (ES) M+H expected=414.2, found 414.2. $^1$H NMR (CDCl$_3$, 400 MHz, 23° C.) δ 7.10-7.14 (m, 2H), 6.99-7.03 (m, 2H), 5.00 (d, J=15.6 Hz, 1H), 4.86 (d, J=15.6 Hz, 1H), 4.32-4.35 (m, 1H), 3.64-6.68 (m, 1H), 3.42-3.50 (m, 1H), 2.96-3.03 (m, 1H), 2.74 (s, 2H), 2.26 (s, 3H), 1.55-1.61 (m, 4H), 1.23 (s, 1H).

Example 7

1-[4-(4-Fluoro-benzyl)-4-hydroxy-piperidin-1-yl]-2-pyrazolo[3,4-b]pyridin-1-ylethanone

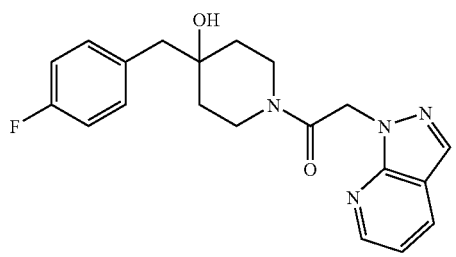

The title compound was prepared according to the procedure described in EXAMPLE 1 using pyrazolo[3,4-b]pyridin-1-yl-acetic acid. MS (ES) [M+H]$^+$ expected 369.2, found 369.2.

Synthesis of Intermediates (1)

Preparation of 4-(4-Fluoro-benzyl)-piperidine-4-Carboxylic acid ethyl ester

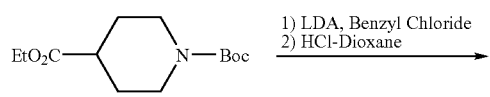

To a solution of LDA in THF (9.5 mL, 1.80 M) at −78° C. (using a dry ice/acetone bath), was added a solution of piperidine-1,4-dicarboxylic acid 1-tert-butyl ester 4-ethyl ester (4.0 g, 15.5 mmol) in THF (10 mL) slowly over 20 minutes. After stirring for 1 hour, a solution of benzyl chloride (2.36 g, 16.3 mmol) in THF (10 ml) was added dropwise to the reaction mixture over 20 minutes. The resultant mixture was stirred for additional 1 hour and then warmed to ambient temperature. The reaction mixture was diluted with EtOAc, then washed with water and the organic extracts were dried over Na$_2$SO$_4$ to provide the crude product. The crude product with diluted with a solution of HCl in dioxane stirred then concentrated to provide 4-(4-Fluoro-benzyl)-piperidine-4-Carboxylic acid ethyl ester that was used without further purification for next step reaction: LCMS Retention time: 0.269 min., LCMS observed for (M+H)$^+$: 266.

Synthesis of Intermediates (2)

Preparation of 4-(4-Fluoro-benzyl)-piperidine-4-carbonitrile

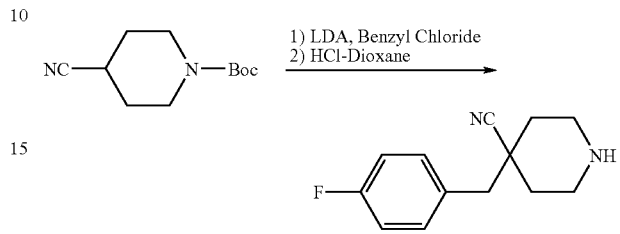

To a solution of LDA in THF (9.5 ml, 1.80 M) cooled in a −78° C. dry ice/acetone bath, was slowly added 4-Cyano-piperidine-1-Carboxylic acid tert-butyl ester (3.26 g, 15.5 mmol) in THF (10 ml) over 20 minutes. After stirring for 1 hour, a solution of benzyl chloride (2.36 g, 16.3 mmol) in THF (10 ml) was added dropwise over 20 minutes. The mixture was stirred for an additional hour and then warmed to ambient temperature. The reaction mixture was diluted with EtOAc, washed with water, dried over Na$_2$SO$_4$, and concentrated in vacuo to provide the crude product. The crude product was diluted with HCl-Dioxane and stirred and concentrated to provide 4-(4-Fluoro-benzyl)-piperidine-4-carbonitrile without further purification for next step reaction: LCMS Retention time: 0.265 min. LCMS observed for (M+H)$^+$: 219.

Biological Example 1

This example illustrates the evaluation of the biological activity associated with compounds of interest of the invention.

Materials and Methods
  A. Cells
    1. CCR1 Expressing Cells
      a) THP-1 Cells THP-1 cells were obtained from ATCC (TIB-202) and cultured as a suspension in RPMI-1640 medium supplemented with 2 mM L-glutamine, 1.5 g/L sodium bicarbonate, 4.5 g/L glucose, 10 mM HEPES, 1 mM sodium pyruvate, 0.05% 2-mercaptoethanol and 10% FBS. Cells were grown under 5% CO$_2$/95% air, 100% humidity at 37° C. and subcultured twice weekly at 1:5 (cells were cultured at a density range of 2×10$^5$ to 2×10$^6$ cells/mL) and harvested at 1×10$^6$ cells/mL. THP-1 cells express CCR1 and can be used in CCR1 binding and functional assays.

b) Isolated Human Monocytes

Monocytes were isolated from human buffy coats using the Miltenyi bead isolation system (Miltenyi, Auburn, Calif.). Briefly, following a Ficoll gradient separation to isolate peripheral blood mononuclear cells, cells were washed with PBS and the red blood cells lysed using standard procedures. Remaining cells were labeled with anti-CD14 antibodies coupled to magnetic beads (Miltenyi Biotech, Auburn, Calif.). Labeled cells were passed through AutoMACS (Miltenyi, Auburn, Calif.) and positive fraction collected. Monocytes express CCR1 and can be used in CCR1 binding and functional assays.

B. Assays

1. Inhibition of CCR1 Ligand Binding

CCR1 expressing cells were centrifuged and resuspended in assay buffer (20 mM HEPES pH 7.1, 140 mM NaCl, 1 mM CaCl$_2$, 5 mM MgCl$_2$, and with 0.2% bovine serum albumin) to a concentration of 5×10$^6$ cells/mL for THP-1 cells and 5×10$^5$ for monocytes. Binding assays were set up as follows. 0.1 mL of cells (5×10$^5$ THP-1 cells/well or 5×10$^4$ monocytes) was added to the assay plates containing the compounds, giving a final concentration of ~2-10 µM each compound for screening (or part of a dose response for compound IC$_{50}$ determinations). Then 0.1 mL of $^{125}$I labeled MIP-1α (obtained from Perkin Elmer Life Sciences, Boston, Mass.) or 0.1 mL of $^{125}$I labeled CCL15/leukotactin (obtained as a custom radiolabeling by Perkin Elmer Life Sciences, Boston, Mass.) diluted in assay buffer to a final concentration of ~50 pM, yielding ~30,000 cpm per well, was added (using $^{125}$I labeled MIP-1α with THP-1 cells and $^{125}$I labeled CCL15/leukotactin with monocytes), the plates sealed and incubated for approximately 3 hours at 4° C. on a shaker platform. Reactions were aspirated onto GF/B glass filters pre-soaked in 0.3% polyethyleneimine (PEI) solution, on a vacuum cell harvester (Packard Instruments; Meriden, Conn.). Scintillation fluid (40 µl; Microscint 20, Packard Instruments) was added to each well, the plates were sealed and radioactivity measured in a Topcount scintillation counter (Packard Instruments). Control wells containing either diluent only (for total counts) or excess MIP-1α or MIP-1β (1 µg/mL, for non-specific binding) were used to calculate the percent of total inhibition for compound. The computer program Prism from GraphPad, Inc. (San Diego, Calif.) was used to calculate IC$_{50}$ values. IC$_{50}$ values are those concentrations required to reduce the binding of labeled MIP-1α to the receptor by 50%. (For further descriptions of ligand binding and other functional assays, see Dairaghi, et al., *J. Biol. Chem.* 274:21569-21574 (1999), Penfold, et al., Proc. Natl. Acad. Sci. USA. 96:9839-9844 (1999), and Dairaghi, et al., *J. Biol. Chem.* 272:28206-28209 (1997)).

2. Calcium Mobilization

To detect the release of intracellular stores of calcium, cells (THP-1 or monocytes) were incubated with 3 µM of INDO-1AM dye (Molecular Probes; Eugene, Oreg.) in cell media for 45 minutes at room temperature and washed with phosphate buffered saline (PBS). After INDO-1AM loading, the cells were resuspended in flux buffer (Hank's balanced salt solution (HBSS) and 1% FBS). Calcium mobilization was measured using a Photon Technology International spectrophotometer (Photon Technology International; New Jersey) with excitation at 350 nm and dual simultaneous recording of fluorescence emission at 400 nm and 490 nm. Relative intracellular calcium levels were expressed as the 400 nm/490 nm emission ratio. Experiments were performed at 37° C. with constant mixing in cuvettes each containing 10$^6$ cells in 2 mL of flux buffer. The chemokine ligands may be used over a range from 1 to 100 nM. The emission ratio was plotted over time (typically 2-3 minutes). Ligand blocking compounds of interest (up to 10 µM) were added at 10 seconds, followed by chemokines at 60 seconds (i.e., MIP-1α; R&D Systems; Minneapolis, Minn.) and control chemokine (i.e., SDF-1α; R&D Systems; Minneapolis, Minn.) at 150 seconds.

3. Chemotaxis Assays

Chemotaxis assays were performed using 5 lm pore polycarbonate, polyvinylpyrrolidone-coated filters in 96-well chemotaxis chambers (Neuroprobe; Gaithersburg, Md.) using chemotaxis buffer (Hank's balanced salt solution (HBSS) and 1% FBS). CCR1 chemokine ligands (i.e., MIP-1α, CCL15/Leukotactin; R&D Systems; Minneapolis, Minn.) are use to evaluate compound mediated inhibition of CCR1 mediated migration. Other chemokines (i.e., SDF-1α; R&D Systems; Minneapolis, Minn.) are used as specificity controls. The lower chamber was loaded with 29 µl of chemokine (i.e., 0.1 nM CCL15/Leukotactin) and varying amounts of compound; the top chamber contained 100,000 THP-1 or monocyte cells in 20 µl. The chambers were incubated 1-2 hours at 37° C., and the number of cells in the lower chamber quantified either by direct cell counts in five high powered fields per well or by the CyQuant assay (Molecular Probes), a fluorescent dye method that measures nucleic acid content and microscopic observation.

C. Identification of Inhibitors of CCR1

1. Assay

To evaluate small organic molecules that prevent the receptor CCR1 from binding ligand, an assay was employed that detected radioactive ligand (i.e., MIP-1α or CCL15/Leukotactin) binding to cells expressing CCR1 on the cell surface (for example, THP-1 cells or isolated human monocytes). For compounds that inhibited binding, whether competitive or not, fewer radioactive counts are observed when compared to uninhibited controls.

THP-1 cells and monocytes lack other chemokine receptors that bind the same set of chemokine ligands as CCR1 (i.e., MIP-1α, MPIF-1, Leukotactin, etc.). Equal numbers of cells were added to each well in the plate. The cells were then incubated with radiolabeled MIP-1α. Unbound ligand was removed by washing the cells, and bound ligand was determined by quantifying radioactive counts. Cells that were incubated without any organic compound gave total counts; non-specific binding was determined by incubating the cells with unlabeled ligand and labeled ligand. Percent inhibition was determined by the equation:

$$\% \text{inhibition} = (1 - [(\text{sample cpm}) - (\text{nonspecific cpm})] / [(\text{total cpm}) - (\text{nonspecific cpm})]) \times 100.$$

2. Dose Response Curves

To ascertain a compound of interest's affinity for CCR1 as well as confirm its ability to inhibit ligand binding, inhibitory activity was titered over a 1×10$^{-10}$ to 1×10$^{-4}$ M range of compound concentrations. In the assay, the amount of compound was varied; while cell number and ligand concentration were held constant.

3. CCR1 Functional Assays

CCR1 is a seven transmembrane, G-protein linked receptor. A hallmark of signaling cascades induced by the ligation of some such receptors is the pulse-like release of calcium ions from intracellular stores. Calcium mobilization assays were performed to determine if the CCR1 inhibitory compounds of interest were able to also block aspects of CCR1 signaling. Compounds of interest able to inhibit ligand binding and signaling with an enhanced specificity over other chemokine and non-chemokine receptors were desired.

Calcium ion release in response to CCR1 chemokine ligands (i.e., MIP-1α, MPIF-1, Leukotactin, etc.) was measured using the calcium indicator INDO-1. THP-1 cells or monocytes were loaded with INDO-1/AM and assayed for calcium release in response to CCR1 chemokine ligand (i.e., MIP-1α) addition. To control for specificity, non-CCR1 ligands, specifically bradykinin, was added, which also signals via a seven transmembrane receptor. Without compound, a pulse of fluorescent signal will be seen upon MIP-1α addition. If a compound specifically inhibits CCR1-MIP-1α signaling, then little or no signal pulse will be seen upon MIP-1α addition, but a pulse will be observed upon bradykinin addition. However, if a compound non-Specifically inhibits signaling, then no pulse will be seen upon both MIP-1α and bradykinin addition.

One of the primary functions of chemokines is their ability to mediate the migration of chemokine receptor-expressing cells, such as white blood cells. To confirm that a compound of interest inhibited not only CCR1 specific binding and signaling (at least as determined by calcium mobilization assays), but also CCR1 mediated migration, a chemotaxis assay was employed. THP-1 myelomonocytic leukemia cells, which resemble monocytes, as wells as freshly isolated monocytes, were used as targets for chemoattraction by CCR1 chemokine ligands (i.e., MIP-1α, CCL15/leukotactin). Cells were place in the top compartment of a microwell migration chamber, while MIP-1α (or other potent CCR1 chemokine ligand) and increasing concentrations of a compound of interest was loaded in the lower chamber. In the absence of inhibitor, cells will migrate to the lower chamber in response to the chemokine agonist; if a compound inhibited CCR1 function, then the majority of cells will remain in the upper chamber. To ascertain a compound of interest's affinity for CCR1 as well as to confirm its ability to inhibit CCR1 mediated cell migration, inhibitory activity was titered over a $1 \times 10^{-10}$ to $1 \times 10^4$ M range of compound concentrations in this chemotaxis assay. In this assay, the amount of compound was varied; while cell number and chemokine agonist concentrations were held constant. After the chemotaxis chambers were incubated 1-2 hours at 37° C., the responding cells in the lower chamber were quantified by labeling with the CyQuant assay (Molecular Probes), a fluorescent dye method that measures nucleic acid content, and by measuring with a Spectrafluor Plus (Tecan). The computer program Prism from GraphPad, Inc. (San Diego, Calif.) was used to calculate $IC_{50}$ values. $IC_{50}$ values are those compound concentrations required to inhibit the number of cells responding to a CCR1 agonist by 50%.

4. In Vivo Efficacy a) Rabbit Model of Destructive Joint Inflammation

To study the effects of compounds of interest on inhibiting the inflammatory response of rabbits to an intra-articular injection of the bacterial membrane component lipopolysaccharide (LPS), a rabbit model of destructive joint inflammation is used. This study design mimics the destructive joint inflammation seen in arthritis. Intra-articular injection of LPS causes an acute inflammatory response characterized by the release of cytokines and chemokines, many of which have been identified in rheumatoid arthritic joints. Marked increases in leukocytes occur in synovial fluid and in synovium in response to elevation of these chemotactic mediators. Selective antagonists of chemokine receptors have shown efficacy in this model (see Podolin, et al., *J Immunol.* 169(11):6435-6444 (2002)).

A rabbit LPS study is conducted essentially as described in Podolin, et al. ibid., female New Zealand rabbits (approximately 2 kilograms) are treated intra-articularly in one knee with LPS (10 ng) together with either vehicle only (phosphate buffered saline with 1% DMSO) or with addition of a compound of interest (dose 1=50 μM or dose 2=100 μM) in a total volume of 1.0 mL. Sixteen hours after the LPS injection, knees are lavaged and cells counts are performed. Beneficial effects of treatment were determined by histopathologic evaluation of synovial inflammation. Inflammation scores are used for the histopathologic evaluation: 1-minimal, 2-mild, 3-moderate, 4-moderate-marked.

b) Evaluation of a Compound of Interest in a Rat Model of Collagen Induced Arthritis A 17 day developing type II collagen arthritis study is conducted to evaluate the effects of a compound of interest on arthritis induced clinical ankle swelling. Rat collagen arthritis is an experimental model of polyarthritis that has been widely used for preclinical testing of numerous anti-arthritic agents (see Trentham, et al., *J. Exp. Med.* 146(3):857-868 (1977), Bendele, et al., *Toxicologic Pathol.* 27:134-142 (1999), Bendele, et al., *Arthritis Rheum.* 42:498-506 (1999)). The hallmarks of this model are reliable onset and progression of robust, easily measurable polyarticular inflammation, marked cartilage destruction in association with pannus formation and mild to moderate bone resorption and periosteal bone proliferation.

Female Lewis rats (approximately 0.2 kilograms) are anesthetized with isoflurane and injected with Freund's Incomplete Adjuvant containing 2 mg/mL bovine type II collagen at the base of the tail and two sites on the back on days 0 and 6 of this 17 day study. A compound of interest is dosed daily in a sub-cutaneous manner from day 0 till day 17 at a efficacious dose. Caliper measurements of the ankle joint diameter were taken, and reducing joint swelling is taken as a measure of efficacy.

In the table below, structures and activity are provided for representative compounds described herein. Activity is provided as follows for either the chemotaxis assay or binding assay as described above: ++, $IC_{50} \geq 25000$ nM; +++, 1000 nM<$IC_{50}$<25000 nM; and ++++, $IC_{50}$<1000 nM.

TABLE 2

Structure

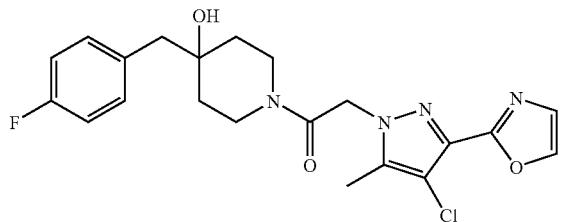

Example 1/++++

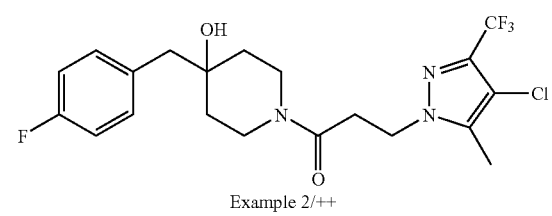

Example 2/++

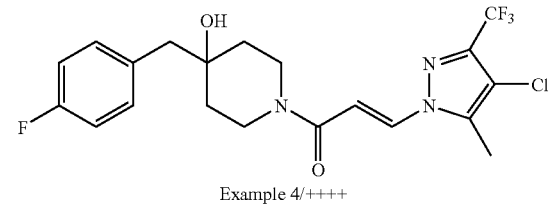

Example 4/++++

TABLE 2-continued

| Structure |
|---|
| Example 5/++ |
| Example 7/+++ |
| Example 6/+++ |

All patents, patent applications, publications and presentations referred to herein are incorporated by reference in their entirety. Any conflict between any reference cited herein and the teaching of this specification is to be resolved in favor of the latter. Similarly, any conflict between an art-recognized definition of a word or phrase and a definition of the word or phrase as provided in this specification is to be resolved in favor of the latter.

What is claimed is:

1. A compound having formula I (I)

and pharmaceutically acceptable salts and N-oxides thereof; wherein $R^{2a}$, $R^{2b}$, $R^{2c}$, $R^{2d}$ and $R^{2e}$ are each independently selected from the group consisting of hydrogen, halogen, —$OR^c$, —$R^e$ and CN, wherein each $R^c$ is independently selected from hydrogen, $C_{1-8}$ alkyl, and $C_{1-8}$ haloalkyl; and each $R^e$ is independently selected from the group consisting of $C_{1-8}$ alkyl and $C_{1-8}$ haloalkyl, and at least one of $R^{2a}$, $R^{2b}$, $R^{2c}$, $R^{2d}$ and $R^{2e}$ is other than hydrogen;

B is pyrazolyl and is substituted with 0 to 3 $R^3$ substituents, and at each occurrence, $R^3$ is independently selected from the group consisting of halogen, —$R^h$, —CN and —Y, wherein Y is a member selected from the group consisting of oxazolyl, pyridyl, pyrimidinyl, oxadiazolyl and thiazolyl and each $R^h$ is independently selected from the group consisting of $C_{1-8}$ alkyl and $C_{1-8}$ haloalkyl;

$L^1$ is a linking group selected from the group consisting of $C_{1-4}$ alkylene and $C_{2-4}$ alkenylene; and A is a member selected from the group consisting of hydrogen and —$OR^q$, wherein $R^q$ is selected from the group consisting of hydrogen, $C_{1-8}$ alkyl and $C_{1-8}$ haloalkyl.

2. The compound of claim 1, wherein B is pyrazolyl and is substituted with 1-3 $R^3$.

3. The compound of claim 2, wherein the pyrazolyl group is linked to the remainder of the molecule via a nitrogen atom ring member.

4. The compound of claim 1, wherein A is selected from the group consisting of H and OH.

5. The compound of claim 1, wherein each $R^3$ is independently selected from the group consisting of hydrogen, chloro, fluoro, bromo, oxazolyl, pyridyl, pyrimidinyl, oxadiazolyl, thiazolyl, —$R^h$ and cyano.

6. The compound of claim 5, wherein each $R^3$ is independently selected from the group consisting of fluoro, chloro, bromo, $C_{1-4}$ alkyl and $C_{1-4}$ haloalkyl.

7. The compound of claim 1, wherein
$R^{2a}$ is a member selected from the group consisting of hydrogen and halogen;
$R^{2b}$ and $R^{2e}$ are each hydrogen;
$R^{2c}$ and $R^{2d}$ are each independently selected from the group consisting of hydrogen, halogen, —$OR^c$ and —CN.

8. The compound of claim 7, wherein $R^{2a}$, $R^{2b}$, $R^{2d}$ and $R^{2e}$ are each hydrogen; and $R^{2c}$ is selected from the group consisting of halogen and —CN.

9. The compound of claim 8, wherein $R^{2c}$ is fluoro, chloro, or iodo.

10. The compound of claim 7, wherein $R^{2a}$, $R^{2b}$, $R^{2e}$ are each hydrogen.

11. The compound of claim 7, wherein $R^{2c}$ is Cl or F.

12. The compound of claim 1, wherein A is hydrogen or hydroxy; $L^1$ is selected from the group consisting of —$CH_2$—, —$CH_2CH_2$— and —CH=CH—; and B is a pyrazolyl ring attached to the remainder of the molecule via a nitrogen atom ring member.

13. The compound of claim 12, wherein $R^{2a}$, $R^{2b}$ and $R^{2e}$ are each hydrogen and $R^{2c}$ and $R^{2d}$ are each selected from the group consisting of hydrogen, halogen, —$OR^c$, —$R^e$, and CN.

14. The compound of claim 13, wherein $R^{2c}$ is Cl or F.

15. The compound of claim 1, wherein said compound is selected from the group consisting of:
2-(4-Chloro-5-methyl-3-trifluoromethyl-pyrazol-1-yl)-1-[4-(4-fluoro-benzyl)-4-hydroxy-piperidin-1-yl]-ethanone and
2-(4-Chloro-5-methyl-3-oxazol-2-yl-pyrazol-1-yl)-1-[4-(4-fluoro-benzyl)-4-hydroxy-piperidin-1-yl]-ethanone.

16. The compound of claim 1, wherein said compound is selected from the group consisting of:

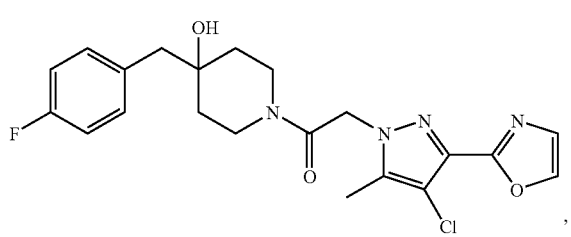
,
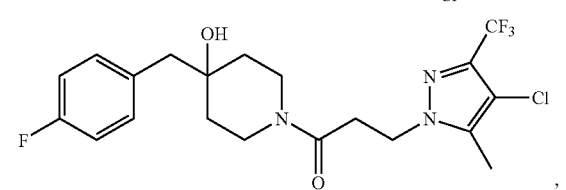
,
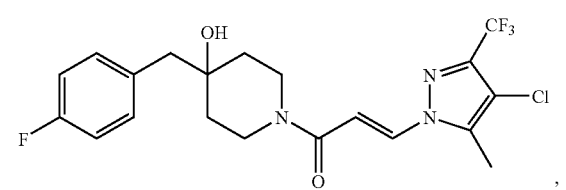
,
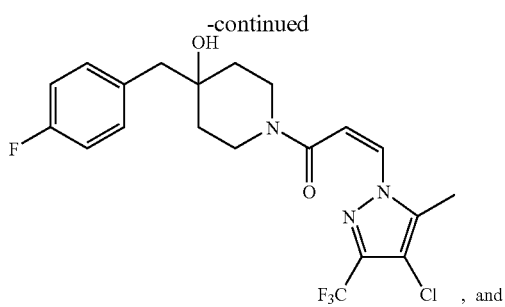
, and
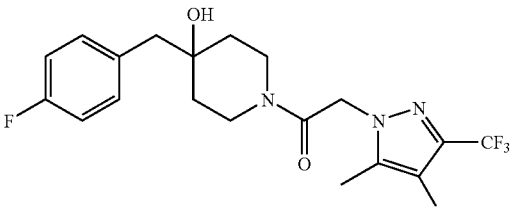
.
17. A pharmaceutical composition comprising a pharmaceutically acceptable excipient or carrier and a compound of any of claims 1, 2, 3, 4, 5-10, 11-14, 15 or 16.
* * * * *

UNITED STATES PATENT AND TRADEMARK OFFICE
CERTIFICATE OF CORRECTION

PATENT NO. : 7,576,106 B2
APPLICATION NO. : 11/580202
DATED : August 18, 2009
INVENTOR(S) : Zhang et al.

It is certified that error appears in the above-identified patent and that said Letters Patent is hereby corrected as shown below:

Title Page:

Face sheet, Section (56), "FOREIGN PATENT DOCUMENTS" subsection, fourth cite, please delete "WO 01/90101" and insert --WO 01/090101--.

In the Claims:

Claim 13, Column 42, Line 56: please insert a bond dash before "CN" (so that it reads: --CN).

Signed and Sealed this

Fifteenth Day of June, 2010

David J. Kappos
*Director of the United States Patent and Trademark Office*